US009144646B2

(12) United States Patent
Barron, III et al.

(10) Patent No.: US 9,144,646 B2
(45) Date of Patent: Sep. 29, 2015

(54) VIAL SPIKING DEVICES AND RELATED ASSEMBLIES AND METHODS

(71) Applicant: Fresenius Medical Care Holdings, Inc., Waltham, MA (US)

(72) Inventors: John A. Barron, III, Seven Fields, PA (US); Chad Unger, Verona, PA (US); Douglas Mark Zatezalo, Allison Park, PA (US); Michael John Zang, Allison Park, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 240 days.

(21) Appl. No.: 13/801,028

(22) Filed: Mar. 13, 2013

(65) Prior Publication Data

US 2013/0289515 A1    Oct. 31, 2013

Related U.S. Application Data

(60) Provisional application No. 61/638,163, filed on Apr. 25, 2012.

(51) Int. Cl.
*A61J 1/10* (2006.01)
*A61M 5/162* (2006.01)
(Continued)

(52) U.S. Cl.
CPC .............. *A61M 5/162* (2013.01); *A61J 1/1406* (2013.01); *A61J 1/2089* (2013.01); *A61J 1/1418* (2015.05);
(Continued)

(58) Field of Classification Search
CPC .............. A61J 1/14; A61J 1/1475; A61J 1/20; A61J 1/2089; A61J 1/2096; A61J 2001/1481; A61J 2001/1487; A61J 2001/2006; A61J 2001/201; A61J 2001/2065; Y10S 604/905; F16L 33/00; F16L 33/02; F16L 33/28
See application file for complete search history.

(56) References Cited

U.S. PATENT DOCUMENTS 3,734,080 A   5/1973   Petterson et al.
4,775,369 A   10/1988  Schwartz
(Continued)

FOREIGN PATENT DOCUMENTS

EP    0146310 A1    6/1985
EP    0426273       5/1991
(Continued)

OTHER PUBLICATIONS

International Search Report and Written Opinion from PCT Application No. PCT/US2010/040547, mailed Oct. 29, 2010, pp. 1-12.
(Continued)

*Primary Examiner* — Philip R Wiest
*Assistant Examiner* — Benjamin Klein
(74) *Attorney, Agent, or Firm* — Fish & Richardson P.C.

(57) ABSTRACT

In some aspects, a vial spiking device includes a base, a spike extending from the base, and a side wall extending from the base and substantially surrounding the spike. The base and the side wall partially define a recess to receive a portion of a vial. Resilient fingers extend inwardly from the side wall into the recess. The fingers are spaced circumferentially around the side wall and are configured so that as the vial is inserted into the recess, the fingers deflect toward the side wall and allow the portion of the vial to move beyond the fingers. The fingers rebound into the recess after the portion of the vial has moved beyond the fingers. The side wall forces the portion of the vial away from the base and into contact with the fingers after the fingers have rebounded into the recess.

42 Claims, 17 Drawing Sheets

(51) Int. Cl.
*A61J 1/14* (2006.01)
*A61J 1/20* (2006.01)
*A61J 1/18* (2006.01)
*A61M 39/10* (2006.01)

(52) U.S. Cl.
CPC . *A61J 1/1481* (2015.05); *A61J 1/18* (2013.01); *A61J 1/201* (2015.05); *A61J 1/2055* (2015.05); *A61M 2039/1072* (2013.01)

(56) References Cited

U.S. PATENT DOCUMENTS

| | | | |
|---|---|---|---|
| 4,850,972 A | 7/1989 | Schulman et al. | |
| 4,898,578 A | 2/1990 | Rubalcaba | |
| 4,915,688 A | 4/1990 | Bischof et al. | |
| 4,925,444 A | 5/1990 | Orkin et al. | |
| 4,943,279 A | 7/1990 | Samiotes et al. | |
| 4,946,439 A | 8/1990 | Eggers | |
| 4,959,050 A | 9/1990 | Bobo | |
| 4,966,579 A | 10/1990 | Polaschegg | |
| 4,981,467 A | 1/1991 | Bobo et al. | |
| 5,037,390 A | 8/1991 | Raines et al. | |
| 5,041,086 A | 8/1991 | Koenig et al. | |
| 5,047,014 A | 9/1991 | Mosebach et al. | |
| 5,049,129 A | 9/1991 | Zdeb et al. | |
| 5,053,019 A | 10/1991 | Duffy | |
| 5,057,076 A | 10/1991 | Polaschegg | |
| 5,074,756 A | 12/1991 | Davis | |
| 5,078,683 A | 1/1992 | Sancoff et al. | |
| 5,102,392 A | 4/1992 | Sakai et al. | |
| 5,122,123 A | 6/1992 | Vaillancourt | |
| 5,122,129 A | 6/1992 | Olson et al. | |
| 5,127,618 A | 7/1992 | Page et al. | |
| 5,169,388 A | 12/1992 | McPhee | |
| 5,176,631 A | 1/1993 | Koenig | |
| 5,193,990 A | 3/1993 | Kamen et al. | |
| 5,207,642 A | 5/1993 | Orkin et al. | |
| 5,211,201 A | 5/1993 | Kamen et al. | |
| 5,213,483 A | 5/1993 | Flaherty et al. | |
| 5,246,347 A | 9/1993 | Davis | |
| 5,252,044 A | 10/1993 | Raines et al. | |
| 5,256,157 A | 10/1993 | Samiotes et al. | |
| 5,304,126 A | 4/1994 | Epstein et al. | |
| 5,304,165 A | 4/1994 | Haber et al. | |
| 5,317,506 A | 5/1994 | Coutre et al. | |
| 5,324,258 A | 6/1994 | Rohrbough | |
| 5,329,976 A | 7/1994 | Haber et al. | |
| 5,378,231 A | 1/1995 | Johnson et al. | |
| 5,382,232 A | 1/1995 | Hague et al. | |
| 5,392,638 A | 2/1995 | Kawahara | |
| 5,401,237 A | 3/1995 | Tachibana et al. | |
| 5,421,812 A | 6/1995 | Langley et al. | |
| 5,431,626 A | 7/1995 | Bryant et al. | |
| 5,431,627 A | 7/1995 | Pastrone et al. | |
| 5,438,510 A | 8/1995 | Bryant et al. | |
| 5,445,621 A | 8/1995 | Poli et al. | |
| 5,464,392 A | 11/1995 | Epstein et al. | |
| 5,494,822 A | 2/1996 | Sadri | |
| 5,496,273 A | 3/1996 | Pastrone et al. | |
| 5,531,697 A | 7/1996 | Olsen et al. | |
| 5,531,698 A | 7/1996 | Olsen | |
| 5,533,389 A | 7/1996 | Kamen et al. | |
| 5,547,470 A | 8/1996 | Johnson et al. | |
| 5,552,118 A | 9/1996 | Mayer | |
| 5,573,502 A | 11/1996 | LeCocq et al. | |
| 5,575,310 A | 11/1996 | Kamen et al. | |
| 5,578,223 A | 11/1996 | Bene et al. | |
| 5,609,575 A | 3/1997 | Larson et al. | |
| 5,616,124 A | 4/1997 | Hague et al. | |
| 5,641,892 A | 6/1997 | Larkins et al. | |
| 5,643,218 A | 7/1997 | Lynn et al. | |
| 5,651,775 A | 7/1997 | Walker et al. | |
| 5,698,090 A | 12/1997 | Bene et al. | |
| 5,713,865 A | 2/1998 | Manning et al. | |
| 5,743,886 A | 4/1998 | Lynn et al. | |
| 5,745,378 A | 4/1998 | Barker et al. | |
| 5,752,931 A | 5/1998 | Nazarian et al. | |
| 5,755,563 A | 5/1998 | Clegg et al. | |
| 5,785,701 A | 7/1998 | Sams et al. | |
| 5,800,387 A | 9/1998 | Duffy et al. | |
| 5,816,779 A | 10/1998 | Lawless et al. | |
| 5,843,035 A | 12/1998 | Bowman et al. | |
| 5,873,872 A | 2/1999 | Thibault et al. | |
| 5,897,526 A | 4/1999 | Vaillancourt | |
| 5,916,197 A | 6/1999 | Reilly et al. | |
| 5,925,011 A | 7/1999 | Faict et al. | |
| 5,935,099 A | 8/1999 | Peterson et al. | |
| 5,935,105 A | 8/1999 | Manning et al. | |
| 5,938,636 A | 8/1999 | Kramer et al. | |
| 5,941,848 A | 8/1999 | Nishimoto et al. | |
| 5,989,237 A * | 11/1999 | Fowles et al. | 604/413 |
| 5,989,423 A | 11/1999 | Kamen et al. | |
| 6,017,318 A | 1/2000 | Gauthier et al. | |
| 6,019,750 A | 2/2000 | Fowles et al. | |
| 6,041,801 A | 3/2000 | Gray et al. | |
| 6,065,941 A | 5/2000 | Gray et al. | |
| 6,068,612 A | 5/2000 | Bowman et al. | |
| 6,070,761 A | 6/2000 | Bloom et al. | |
| 6,077,246 A | 6/2000 | Kullas et al. | |
| 6,099,492 A | 8/2000 | Le | |
| 6,110,153 A | 8/2000 | Davis et al. | |
| 6,117,103 A | 9/2000 | Tverskoy et al. | |
| 6,123,686 A | 9/2000 | Olsen et al. | |
| 6,126,637 A | 10/2000 | Kriesel et al. | |
| 6,142,008 A | 11/2000 | Cole et al. | |
| 6,210,361 B1 | 4/2001 | Kamen et al. | |
| 6,241,704 B1 | 6/2001 | Peterson et al. | |
| 6,269,340 B1 | 7/2001 | Ford et al. | |
| 6,299,131 B1 | 10/2001 | Ryan | |
| 6,302,653 B1 | 10/2001 | Bryant et al. | |
| 6,321,941 B1 | 11/2001 | Argentieri et al. | |
| 6,416,718 B1 | 7/2002 | Maiefski et al. | |
| 6,464,667 B1 | 10/2002 | Kamen et al. | |
| 6,468,242 B1 | 10/2002 | Wilson et al. | |
| 6,471,872 B2 | 10/2002 | Kitaevich et al. | |
| 6,475,180 B2 | 11/2002 | Peterson et al. | |
| 6,489,896 B1 | 12/2002 | Platt et al. | |
| 6,527,758 B2 | 3/2003 | Ko | |
| 6,575,930 B1 | 6/2003 | Trombley et al. | |
| 6,604,908 B1 | 8/2003 | Bryant et al. | |
| 6,610,024 B1 | 8/2003 | Benatti | |
| 6,616,633 B1 | 9/2003 | Butterfield et al. | |
| 6,622,542 B2 | 9/2003 | Derek et al. | |
| 6,658,396 B1 | 12/2003 | Tang et al. | |
| 6,692,478 B1 | 2/2004 | Paradis | |
| 6,695,803 B1 | 2/2004 | Robinson et al. | |
| 6,699,230 B2 | 3/2004 | Jaafar et al. | |
| 6,726,656 B2 | 4/2004 | Kamen et al. | |
| 6,731,971 B2 | 5/2004 | Evans et al. | |
| 6,736,972 B1 | 5/2004 | Matson | |
| 6,780,322 B1 | 8/2004 | Bissler et al. | |
| 6,802,892 B2 | 10/2004 | Newman et al. | |
| 6,877,713 B1 | 4/2005 | Gray et al. | |
| 6,985,870 B2 | 1/2006 | Martucci et al. | |
| 6,986,759 B1 | 1/2006 | Jeremijevic | |
| 7,029,456 B2 | 4/2006 | Ware et al. | |
| 7,060,049 B2 | 6/2006 | Trombley et al. | |
| 7,074,216 B2 | 7/2006 | Fowles et al. | |
| 7,092,796 B2 | 8/2006 | Vanderveen | |
| 7,128,105 B2 | 10/2006 | Tribble et al. | |
| 7,150,735 B2 | 12/2006 | Hickle | |
| 7,204,823 B2 | 4/2007 | Estes et al. | |
| 7,214,210 B2 | 5/2007 | Kamen et al. | |
| 7,326,186 B2 | 2/2008 | Trombley et al. | |
| 7,338,470 B2 | 3/2008 | Katz et al. | |
| 7,347,849 B2 | 3/2008 | Brugger et al. | |
| 7,427,281 B2 | 9/2008 | Uber | |
| 7,517,332 B2 | 4/2009 | Tonelli et al. | |
| 7,559,524 B2 | 7/2009 | Gray et al. | |
| 7,575,567 B2 | 8/2009 | Simpkins | |
| 7,628,184 B2 | 12/2009 | Py et al. | |
| 7,632,078 B2 | 12/2009 | Demers et al. | |
| 7,641,626 B2 | 1/2010 | Tonelli et al. | |
| 7,654,976 B2 | 2/2010 | Peterson et al. | |

(56) References Cited

U.S. PATENT DOCUMENTS

| | | |
|---|---|---|
| 7,662,139 B2 | 2/2010 | Demers et al. |
| 7,668,731 B2 | 2/2010 | Martucci et al. |
| 7,699,806 B2 | 4/2010 | Ware et al. |
| 7,762,989 B2 | 7/2010 | Simpson |
| 7,766,873 B2 | 8/2010 | Moberg et al. |
| 7,815,621 B2 | 10/2010 | Mann et al. |
| 7,837,647 B2 | 11/2010 | Estes et al. |
| 7,837,651 B2 | 11/2010 | Bishop et al. |
| 7,905,861 B2 | 3/2011 | Rhinehart et al. |
| 7,922,708 B2 | 4/2011 | Estes et al. |
| 7,967,783 B2 | 6/2011 | Rebours |
| 7,967,785 B2 | 6/2011 | Morgan et al. |
| 7,981,101 B2 | 7/2011 | Walsh |
| 7,981,280 B2 | 7/2011 | Carr et al. |
| 7,985,198 B2 | 7/2011 | Von Blumenthal et al. |
| 7,998,115 B2 | 8/2011 | Bedingfield |
| 2002/0045571 A1 | 4/2002 | Liu et al. |
| 2002/0127150 A1* | 9/2002 | Sasso .................. 422/103 |
| 2003/0153895 A1 | 8/2003 | Leinsing |
| 2003/0191445 A1 | 10/2003 | Wallen et al. |
| 2004/0182471 A1 | 9/2004 | Hansen |
| 2005/0085760 A1 | 4/2005 | Ware et al. |
| 2005/0203329 A1 | 9/2005 | Muto et al. |
| 2005/0209563 A1 | 9/2005 | Hopping et al. |
| 2005/0230292 A1 | 10/2005 | Beden et al. |
| 2006/0025747 A1 | 2/2006 | Sullivan et al. |
| 2006/0084905 A1 | 4/2006 | Montgomery et al. |
| 2006/0089594 A1 | 4/2006 | Landau |
| 2006/0229557 A1 | 10/2006 | Fathallah et al. |
| 2007/0062605 A1 | 3/2007 | Wilson et al. |
| 2007/0156089 A1 | 7/2007 | Yu |
| 2008/0242915 A1 | 10/2008 | Jackson et al. |
| 2008/0300570 A1 | 12/2008 | Fowles et al. |
| 2008/0311007 A1 | 12/2008 | Helmerson |
| 2009/0036864 A1 | 2/2009 | Moy et al. |
| 2009/0057258 A1 | 3/2009 | Tornqvist |
| 2009/0069783 A1 | 3/2009 | Ellstrom et al. |
| 2009/0182300 A1 | 7/2009 | Radmer et al. |
| 2009/0204066 A1 | 8/2009 | Radmer et al. |
| 2010/0004602 A1 | 1/2010 | Nord et al. |
| 2010/0030048 A1 | 2/2010 | Heller et al. |
| 2010/0042048 A1 | 2/2010 | Christensen |
| 2010/0084041 A1 | 4/2010 | Fehr et al. |
| 2010/0113891 A1 | 5/2010 | Barrett et al. |
| 2010/0179506 A1 | 7/2010 | Shemesh et al. |
| 2011/0004143 A1 | 1/2011 | Beiriger et al. |
| 2011/0004144 A1 | 1/2011 | Beiriger et al. |
| 2011/0004145 A1 | 1/2011 | Beiriger et al. |
| 2011/0004187 A1 | 1/2011 | Beiriger |
| 2011/0054397 A1 | 3/2011 | Menot et al. |
| 2011/0077614 A1 | 3/2011 | Shay |
| 2011/0094619 A1 | 4/2011 | Steel et al. |
| 2011/0118662 A1 | 5/2011 | Mhatre et al. |
| 2011/0125085 A1 | 5/2011 | McGill et al. |
| 2011/0152770 A1 | 6/2011 | DiPerna et al. |
| 2011/0160701 A1 | 6/2011 | Wyatt et al. |
| 2011/0172603 A1 | 7/2011 | Yodfat et al. |
| 2011/0190702 A1 | 8/2011 | Stumber |
| 2011/0190703 A1 | 8/2011 | Pratt et al. |
| 2012/0209171 A1 | 8/2012 | Vedrine et al. |
| 2013/0018354 A1 | 1/2013 | Sund et al. |

FOREIGN PATENT DOCUMENTS

| | | |
|---|---|---|
| EP | 0532432 | 9/1991 |
| EP | 1978256 | 10/2008 |
| GB | 2098670 | 11/1982 |
| JP | 6346160 A | 2/1988 |
| JP | H01-87740 | 6/1989 |
| JP | 04156849 A | 5/1992 |
| JP | 09299446 A | 11/1997 |
| JP | 2002544439 A | 12/2002 |
| JP | 2003049784 A | 2/2003 |
| JP | 2005160705 A | 6/2005 |
| JP | 2008178444 A | 8/2008 |
| WO | WO9640322 A3 | 3/1997 |
| WO | WO9910027 A1 | 3/1999 |
| WO | WO2006031857 A2 | 3/2006 |
| WO | WO2007101798 A2 | 9/2007 |
| WO | WO2008008845 A2 | 1/2008 |
| WO | WO2008009288 A1 | 1/2008 |
| WO | WO2008064046 A2 | 5/2008 |
| WO | WO2009044221 A1 | 4/2009 |
| WO | WO2010099816 A1 | 9/2010 |
| WO | WO2010100074 A3 | 12/2010 |
| WO | WO2011054693 A1 | 5/2011 |
| WO | WO2011092068 A1 | 8/2011 |

OTHER PUBLICATIONS

International Search Report and Written Opinion from corresponding PCT Application No. PCT/US2013/037922 mailed Jul. 2, 2013, 16 pages.

\* cited by examiner

VIAL SPIKING DEVICES AND RELATED ASSEMBLIES AND METHODS

CROSS-REFERENCE TO RELATED APPLICATIONS

This application claims the benefit of U.S. Provisional Application Ser. No. 61/638,163, filed on Apr. 25, 2012, which is incorporated by reference herein.

TECHNICAL FIELD

This invention relates to vial spiking devices and related assemblies and methods.

BACKGROUND

When kidney failure is diagnosed, patients are typically given medication to help control the symptoms and slow the progress of damage to the kidneys. Patients with chronic kidney failure generally take drugs, such as iron supplements, to control the balance of minerals in the body.

SUMMARY

In an aspect, a vial spiking device includes a base, a spike extending from a central region of the base, a side wall extending from the base and substantially surrounding the spike, the base and the side wall at least partially defining a recess configured to receive a portion of a vial, and a plurality of resilient fingers that extend inwardly from the side wall into the recess. The fingers are spaced circumferentially around the side wall. The fingers are configured so that as the vial is inserted into the recess of the vial spiking device, the fingers deflect toward the side wall and allow the portion of the vial to move beyond the fingers. The fingers are configured to rebound into the recess after the portion of the vial has moved beyond the fingers. The side wall is configured to force the portion of the vial away from the base and into contact with the fingers after the portion of the vial has moved beyond the fingers and the fingers have rebounded into the recess.

Implementations can include one or more of the following features.

In some implementations, the portion of the vial includes a collar disposed around a neck portion of a bottle of the vial.

In some implementations, the portion of the vial includes a cap of the vial.

In some implementations, a lower portion of the side wall of the vial spiking device extends at a first angle relative to a longitudinal axis of the vial spiking device, and the portion of the vial has a surface that extends at a second angle relative to the longitudinal axis of the vial spiking device when the portion of the vial is disposed in the recess of the vial spiking device, and the surface of the portion of the drug vial interfaces with the lower portion of the side wall when the vial is moved into the recess beyond the fingers.

In some implementations, the spike of the vial spiking device is configured so that a seal of the vial is deflected causing an inner surface of the rubber seal to be concave when the vial is forced away from the base and into contact with the fingers.

In some implementations, the fingers are configured to position the vial so that a region along a rubber seal of the vial is positioned over an opening in the spike as the vial is inserted into the recess of the vial spiking device.

In some implementations, the base defines a plurality of holes that permit a fluid to flow in and out of the vial spiking device through the base. In some cases, each of the holes is longitudinally aligned with one of the fingers.

In some implementations, the side wall includes a plurality of side wall segments that are circumferentially spaced around the side wall. In some cases, each of the side wall segments extends at an acute angle relative to the longitudinal axis of the vial spiking device.

In some implementations, a region of the side wall adjacent the base has an inner diameter that is smaller than an outer diameter of the portion of the vial.

In some implementations, the vial is a drug vial.

In some implementations, a tip region of the spike comprises a silicone coating.

In another aspect, a vial spiking device includes a base, a spike extending from a central region of the base, and a side wall extending from the base and substantially surrounding the spike. The base and the side wall at least partially define a recess configured to receive a portion of a vial. The side wall includes a plurality of resilient circumferentially spaced side wall segments that extend at an acute angle relative to a longitudinal axis of the vial spiking device. The side wall segments are configured to deflect away from the longitudinal axis of the vial spiking device when a force is applied to the side wall segments and then rebound toward the longitudinal axis of the vial spiking device when the force is released. A plurality of resilient circumferentially spaced fingers extend from the side wall and are biased into the recess, and the fingers are configured to deflect toward the side wall when a force is applied to the fingers and then rebound away from the side wall when the force is released.

Implementations can include one or more of the following features.

In some implementations, the portion of the vial includes a collar disposed around a neck portion of a bottle of the vial.

In some implementations, the portion of the vial includes a cap of the vial.

In some implementations, a lower portion of the side wall of the vial spiking device extends at a first angle relative to a longitudinal axis of the vial spiking device, and the portion of the vial has a surface that extends at a second angle relative to the longitudinal axis of the vial spiking device when the portion of the vial is disposed in the recess of the vial spiking device, and the surface of the portion of the drug vial interfaces with the lower portion of the side wall when the vial is moved into the recess beyond the fingers.

In some implementations, the spike of the vial spiking device is configured so that a seal of the vial is deflected causing an inner surface of the rubber seal to be concave when the vial is forced away from the base and into contact with the fingers.

In some implementations, the fingers are configured to position the vial so that a region along a rubber seal of the vial is positioned over an opening in the spike as the vial is inserted into the recess of the vial spiking device.

In some implementations, the base defines a plurality of holes that permit a fluid to flow in and out of the vial spiking device through the base. In some cases, each of the holes is longitudinally aligned with one of the fingers.

In some implementations, the side wall includes a plurality of side wall segments that are circumferentially spaced around the side wall.

In some implementations, each of the side wall segments extends at an acute angle relative to the longitudinal axis of the vial spiking device.

In some implementations, a region of the side wall adjacent the base has an inner diameter that is smaller than an outer diameter of the portion of the vial.

In some implementations, the vial is a drug vial.

In some implementations, a tip region of the spike comprises a silicone coating.

In an additional aspect, a vial spiking assembly includes a vial spiking device and a gas-impermeable spike cover. The vial spiking device includes a base defining a plurality of holes, a spike extending from a central region of the base, and a side wall extending from the base and substantially surrounding the spike. The base and the side wall at least partially define a recess configured to receive a portion of a vial. The gas-impermeable spike cover defines a cavity configured to receive the spike, where a portion of the spike cover is configured to be received in the recess and to be retained within the recess. When the spike cover is retained within the recess, fluid can enter and exit the recess through the holes defined by the base of the vial spiking device.

Implementations can include one or more of the following features.

In some implementations, the recess is defined by the side wall.

In some implementations, the holes are circumferentially spaced around the base.

In some implementations, the holes are about equally spaced around the base.

In some implementations, the spike cover defines an opening extending into the cavity and is configured to permit fluid to enter and exit the cavity by passing through the opening.

In some implementations, the spike cover is formed of one or more gas-impermeable materials.

In some implementations, the side wall includes a plurality of resilient circumferentially spaced side wall segments.

In some implementations, the vial spiking assembly also includes a plurality of resilient fingers that extend radially inward from the side wall.

In some implementations, the fingers are configured to retain the spike cover.

In some implementations, each of the fingers is longitudinally aligned with one of the holes in the base.

In some implementations, the vial is a drug vial.

In some implementations, a tip region of the spike comprises a silicone coating.

In a further aspect, a method includes pushing a portion of a vial into a recess defined by a base and a side wall of a vial spiking device such that resilient circumferentially spaced fingers extending from the side wall of the vial spiking device move radially outward and then, after the portion of the vial has moved beyond the fingers, rebound radially inward. The method further includes applying a force to the vial that causes the vial to move away from the base and into contact with the fingers.

Implementations can include one or more of the following features.

In some implementations, the force to the vial is applied by the side wall of the vial spiking device. In some cases, the side wall of the vial spiking device forces the vial away from the base so that a seal of the vial is deflected causing an inner surface of the seal to be concave.

In some implementations, the fingers align a seal of the vial with an opening in a spike extending from the base of the drug vial spiking device.

In some implementations, the fingers are configured to position the vial so that a region along a seal of the vial is disposed along an opening in a spike protruding from the base.

In some implementations, the vial is pushed into the recess until the vial contacts the base of the vial spiking device.

In some implementations, when the vial moves away from the base, a collar of the vial contacts an underside of the fingers.

In some implementations, the fingers are deflected to be substantially parallel to the base.

In another aspect, a method includes causing a sterilizing fluid to flow through holes defined in a base of a vial spiking device. The sterilizing fluid then flows into a cavity defined by a gas-impermeable spike cover disposed on a spike that extends from the base of the vial spiking device, and then the fluid then flows back out of the cavity and back through the holes defined in the base.

Implementations can include one or more of the following features.

In some implementations, the sterilizing fluid enters and exits the cavity substantially only through the holes. In some cases, the sterilizing fluid includes a gas. In some cases, the sterilizing fluid includes ethylene oxide.

In some implementations, the vial spiking device includes retaining features that retain the spike cover in the vial spiking device. In some cases, the retaining features are resilient fingers extending from a side wall of vial spiking device. In some cases, the retaining features are configured to retain the spike cover in the drug vial spiking device when air that is pressurized to about 1.5 psi enters the holes. In some cases, the retaining features are configured to provide a resisting force of at least 0.75 lbf against the spike cover.

In some implementations, the vial spiking device is disposed in a bag (e.g., a gas permeable bag).

In another aspect of the invention, a vial spiking device includes a base, a spike extending from a central region of the base, and a side wall extending from the base and substantially surrounding the spike. The side wall has a first portion that extends at a first acute angle relative to a longitudinal axis of the spiking device, a second portion that extends at a second acute angle relative to the longitudinal axis of the spiking device, and a third portion that is positioned between the first and second portions and extends at a third acute angle relative to the longitudinal axis of the spiking device. The base and the side wall at least partially define a recess configured to receive a portion of a vial. The third portion of the side wall is configured so that as the vial is inserted into the recess of the vial spiking device, the third portion of the side wall deflects radially outward and allows the portion of the vial to be fully inserted into the recess, and the third portion of the side wall is configured to rebound radially inward and force the vial away from the base when a force applied to the vial to insert the vial into the recess is released.

Implementations can include one or more of the following features.

In some implementations, the third acute angle is greater than the first and second acute angles.

In some implementations, the third acute angle is about 29 degrees to about 31 degrees.

In some implementations, the first acute angle is equal to the second acute angle.

In some implementations, the spiking device further includes a plurality of resilient fingers that extend inwardly from the side wall into the recess. The fingers are spaced circumferentially around the side wall and are configured so that as the vial is inserted into the recess of the vial spiking device, the fingers deflect toward the side wall and allow the portion of the vial to move beyond the fingers. The fingers are also configured to rebound into the recess after the portion of the vial has moved beyond the fingers.

In some implementations, the third portion of the side wall is configured to force the portion of the vial away from the base and into contact with the fingers after the portion of the vial has moved beyond the fingers and the fingers have rebounded into the recess.

In some implementations, the portion of the vial includes a collar disposed around a neck portion of a bottle of the vial.

In some implementations, the spike of the vial spiking device is configured so that a seal of the vial is deflected causing an inner surface of the rubber seal to be concave when the vial is forced away from the base.

In some implementations, the base defines a plurality of holes that permit a fluid to flow in and out of the vial spiking device through the base.

In some implementations, the side wall includes a plurality of side wall segments that are circumferentially spaced around the side wall, and the first, second, and third portions of the side wall are portions of one of the side wall segments.

In some implementations, a region of the side wall adjacent the base has an inner diameter that is smaller than an outer diameter of the portion of the vial.

As used throughout this disclosure, the term drug refers to a wide variety of different substances and materials that can be delivered to a patient, such as pharmaceuticals (e.g., pharmaceuticals associated with dialysis treatments, such as heparin, Venofer®, Epogen®, or Aranesp or other pharmaceuticals, such as chemotherapy pharmaceuticals), supplements (e.g., dietary supplements, medical fluids, such as blood substitutes, or other supplements), vitamins (e.g., Vitamin K, Vitamin D, or other vitamins), and other substances (e.g., fluids, such as saline). These specific substances are provided only as examples and are not intended to limit the scope of the claimed subject matter.

Implementations can include one or more of the following advantages.

The vial spiking devices described herein can help to ensure that substantially all of the liquid (e.g., drug) contained in a vial inserted into a recess of the vial spiking device can be evacuated from the vial. The vial spiking device helps to ensure that a vial is pushed a desired distance outward away from the base after being inserted into the recess. This outward movement helps to ensure that a desired concave shape is formed in the seal for ensuring evacuation of the liquid.

The vial spiking devices described herein can help to ensure that users repeatedly insert a vial at least a desired distance into a vial receiving recess of the vial spiking device. This reduces variation in the distance to which the vial is pushed outwardly away from the base and thus reduces variation in the level of concavity formed by the seal from one user to the next during spiking of the vials. As a result, the variability in the ability of the drug vial spiking device to completely evacuate the drug from the vial from user to user can also be reduced.

The vial spiking devices described herein can allow fluids (e.g., gases) to pass through the base and surround the spike. This allows for sterilization of the vial spiking device without the need to use a spike cover that is gas-permeable. Instead, a low cost gas-impermeable material can be used to form the spike cover. As a result, manufacturing costs for the vial spiking device assembly can be significantly reduced.

Holes arranged along the base positioned below the vial retaining features (e.g., the fingers) can also simplify the manufacturing process (e.g., molding) of the vial spiking device. In particular, the holes can be formed by molding pins that also provide a surface to form the underside of the fingers.

The details of one or more embodiments of the invention are set forth in the accompanying drawings and the description below. Other aspects, features, and advantages will be apparent from the description and drawings, and from the claims.

DETAILED DESCRIPTION

In certain aspects, a vial spiking device (e.g., a drug vial spiking device) includes features that arrange a vial (e.g., a drug vial) inserted into a recess of the vial spiking device so that a seal of the vial assumes a concave shape when liquid (e.g., drug) inside the vial is withdrawn from the vial. The features of the vial spiking device can, for example, push the vial upward and away from a base of the vial spiking device so that the seal of the vial is deflected to form a concave shape. Such a concave shape can increase (e.g., maximize) the amount of the liquid inside the vial that can be withdrawn from the vial. Additionally or alternatively, the vial spiking device can include ventilation holes to permit gases (e.g., sterilization gases) to enter and exit the recess of the vial spiking device while a spike cover is retained on a spike of the vial spiking device. The ventilation holes can permit gas sterilization of the vial spiking device and spike cover even when the spike cover is gas-impermeable.

Figure 1:
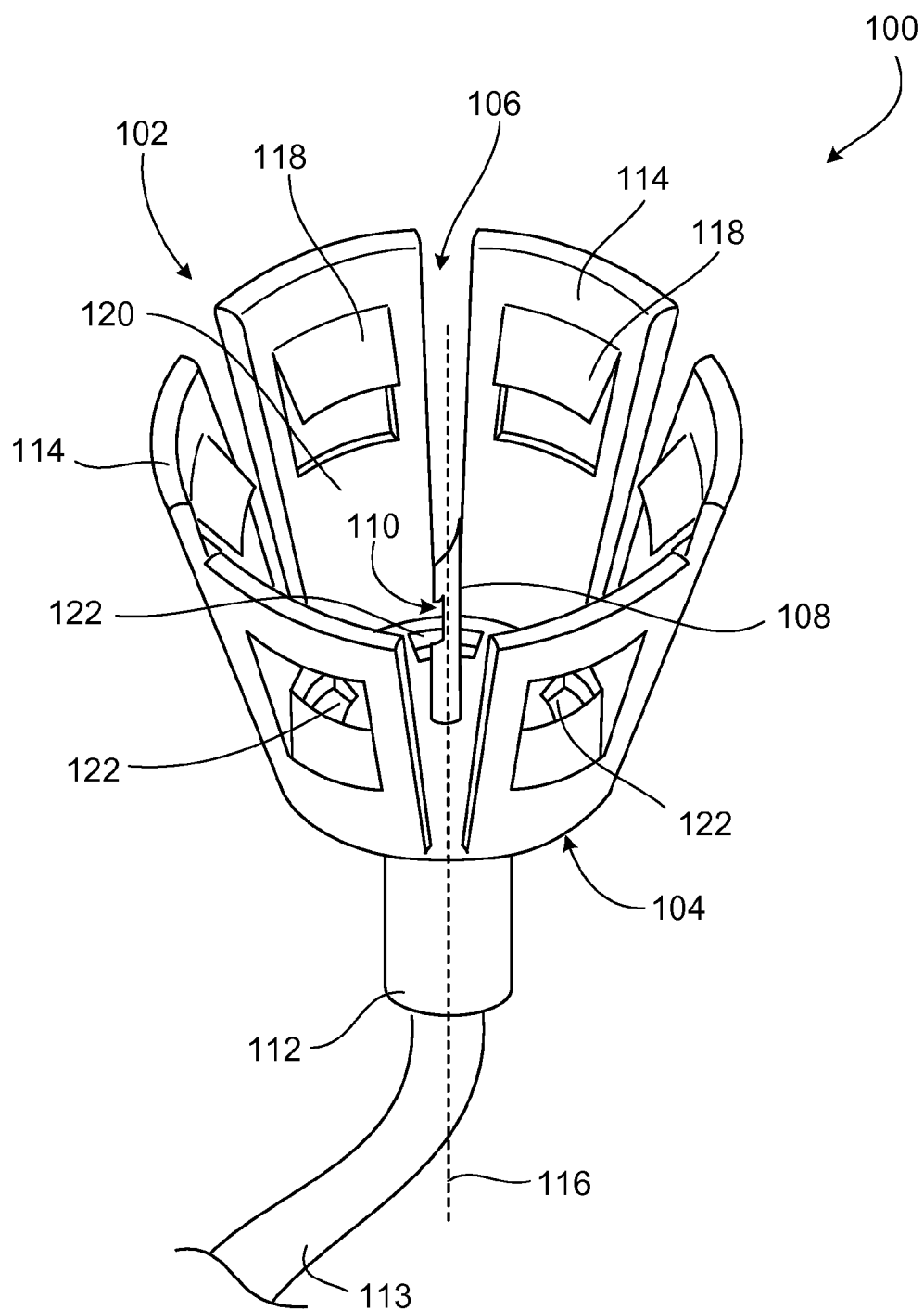
FIG. 1 is a perspective view of a drug vial spiking device that includes a base with ventilation holes and vial retaining features that cause a seal of a vial inserted into the drug vial spiking device to have a concave shape.

Referring to FIG. 1, a drug vial spiking device 100 includes a side wall 102 extending from a peripheral region of a base 104 to form a drug vial receiving recess 106. A spike 108 having a side-opening 110 extends upward from a central region of the base 104. The spike 108 includes a central passage that is in fluid communication with the side-opening 110 and is fluidly connected to an outlet boss 112 extending from a bottom surface of the base 104. The outlet boss 112 is configured to connect to a drug delivery line 113 that delivers drug from a spiked drug vial to a patient. The drug delivery line 113 can, for example, be secured to the outlet boss 112 with a press-fit or a lure-style connection or using adhesives.

The side wall 102 includes six side wall segments 114 that are circumferentially spaced along the side wall 102. Adjacent side wall segments 114 are spaced apart by longitudinal/vertical slots. The side wall segments 114 together with the base 104 form the drug vial receiving recess 106 that is configured to receive a portion of a drug vial (e.g., a collar of a drug vial cap assembly). In some implementations, the drug vial receiving recess 106 is configured to receive a collar having a diameter that is about 0.75 inches to about 1 inch (e.g., about 0.875 inches). The side wall segments 114 extend at an acute angle 121 that is about 13 degrees to about 15 degrees (e.g., about 14 degrees) relative to a longitudinal axis 116 of the drug vial spiking device 100. The side wall segments 114 are configured to deflect away from the longitudinal axis 116 of the drug vial spiking device 100 when a radially outward force is applied (e.g., as a result of the drug vial being inserted into the recess 106) and rebound towards the longitudinal axis 116 when the force is released.

Figure 2:
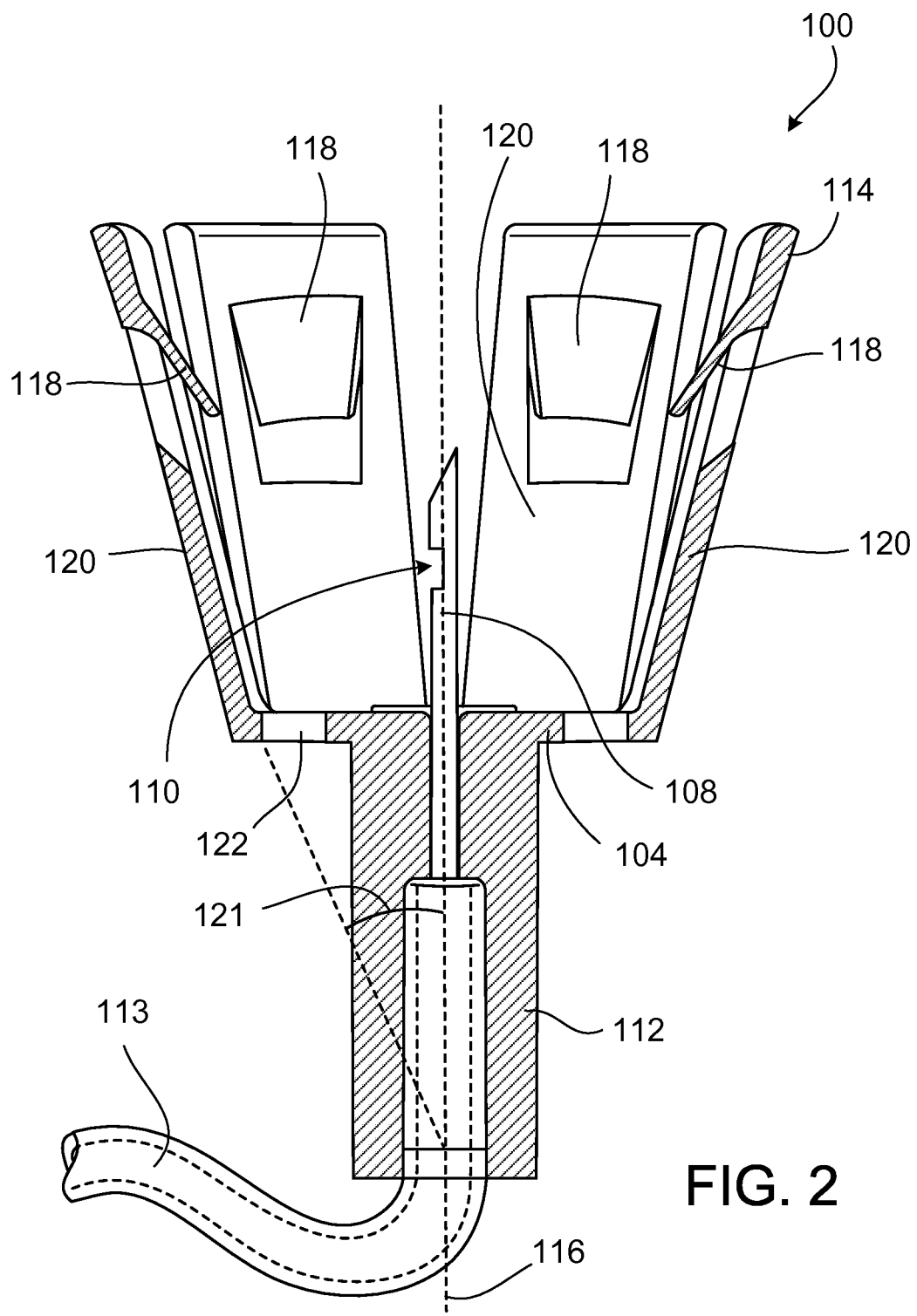
FIG. 2 is a cross-sectional view of the drug vial spiking device of FIG. 1.

Referring to FIGS. 1 and 2, each side wall segment 114 includes a resilient retaining finger 118 extending radially inward (i.e., toward the longitudinal axis 116) from the side wall segment at an angle relative to the longitudinal axis 116. Each finger 118 is biased into the recess 106, is pointed radially inward and toward the base 104, and has an inner, curved surface (i.e., the surface facing the spike 108) having a radius of curvature to accommodate a portion of a drug vial inserted into the drug vial spiking device 100. The fingers 118 are configured so that they can be deflected downward and toward the side wall segments 114 when a force is applied (e.g., as a result of a drug vial being inserted into the recess 106) and rebound away from the side wall 102 (e.g., to their free or biased position) when the force is released. The fingers 118 are configured to provide a variable resisting force that increases as they are deflected further outward and away from their free position. The fingers 118 are also configured to provide a variable resisting force when they are deflected inward towards the longitudinal axis 116 and upward away from the base 104 (e.g., as a result of the vial being pushed upward by the sidewall segments 114 after insertion). The size of the fingers 118 can be adjusted to change the amount of force needed to deflect them. For example, to increase the force needed to deflect the fingers 118, they can be made wider or thicker. In addition, the material properties of the fingers 118 affect the resistance of the fingers to deflection. Thus, to increase the force needed to deflect the fingers 118, a stronger (e.g., stiffer) material can be used. The fingers can be formed of various structurally suitable plastic materials. Examples of suitable materials include polycarbonate, acrylonitrile butadiene styrene (ABS), polypropylene (PP), and polyvinyl chloride (PVC).

The fingers 118 have a sufficient length so that the portion of a vial inserted into the drug vial spiking device 100 travels a desired insertion depth towards the base 104 before it clears the fingers 118 and allows the fingers 118 to rebound towards the longitudinal axis 116. The insertion depth typically corresponds to a convex deflection distance of a seal of the vial when the vial is inserted into the drug vial spiking device 100 (i.e., the distance that the seal deflects when pushed by a spike), for example, as shown in FIG. 6C. The deflection distance can vary based on several factors, such as the material properties of a seal of the vial that is pierced by the spike 108, the size (e.g., diameter and thickness) of the seal, the size (e.g., diameter) of the spike, and the material properties (e.g., smoothness) of the spike. Typically, the insertion depth required to allow the fingers 118 to rebound is at least double the convex deflection distance that the rubber seal deflects as a result of the spike 108 penetrating the rubber seal during spiking.

In some implementations, the fingers 118 have a length that is about 0.1 inches to about 0.2 inches (e.g., about 0.150 inches), a thickness that is about 0.010 inches to about 0.020 inches (e.g., 0.015 inches), and an inner curvature of the fingers 118 has a radius that is about 0.35 inches. In some implementations, the angle at which each of the fingers 118 extends relative to the longitudinal axis 116 can be about 20 degrees to about 21 degrees (e.g., about 21.5 degrees). For example, for a seal made of a flexible material, such as rubber that has a plug diameter (i.e., the diameter of the portion of the seal that is inserted into a vial) of about 0.295 inches to about 0.305 inches and a thickness of about 0.118 inches to about 0.188 inches (e.g., about 0.14 inches), the deflection distance is about 0.050 inches.

Still referring to FIGS. 1 and 2, each side wall segment includes a lower portion 120 that extends upward from the base 104 and is configured to force the vial 150 away from the base 104 after the vial has been inserted into the recess 106 of the drug vial spiking device 100 and the fingers 118 have cleared the back side of the vial collar 152. To force the vial 150 away from the base 104 (i.e., upward in the view shown in FIG. 2), the lower portion 120 extends at an angle 121 relative to the longitudinal axis 116 and is configured to interface with a surface of the portion of the vial 150 that is received in the drug vial receiving recess 116 (e.g., a surface of the vial collar 152 of the vial 150).

Figure 6A:
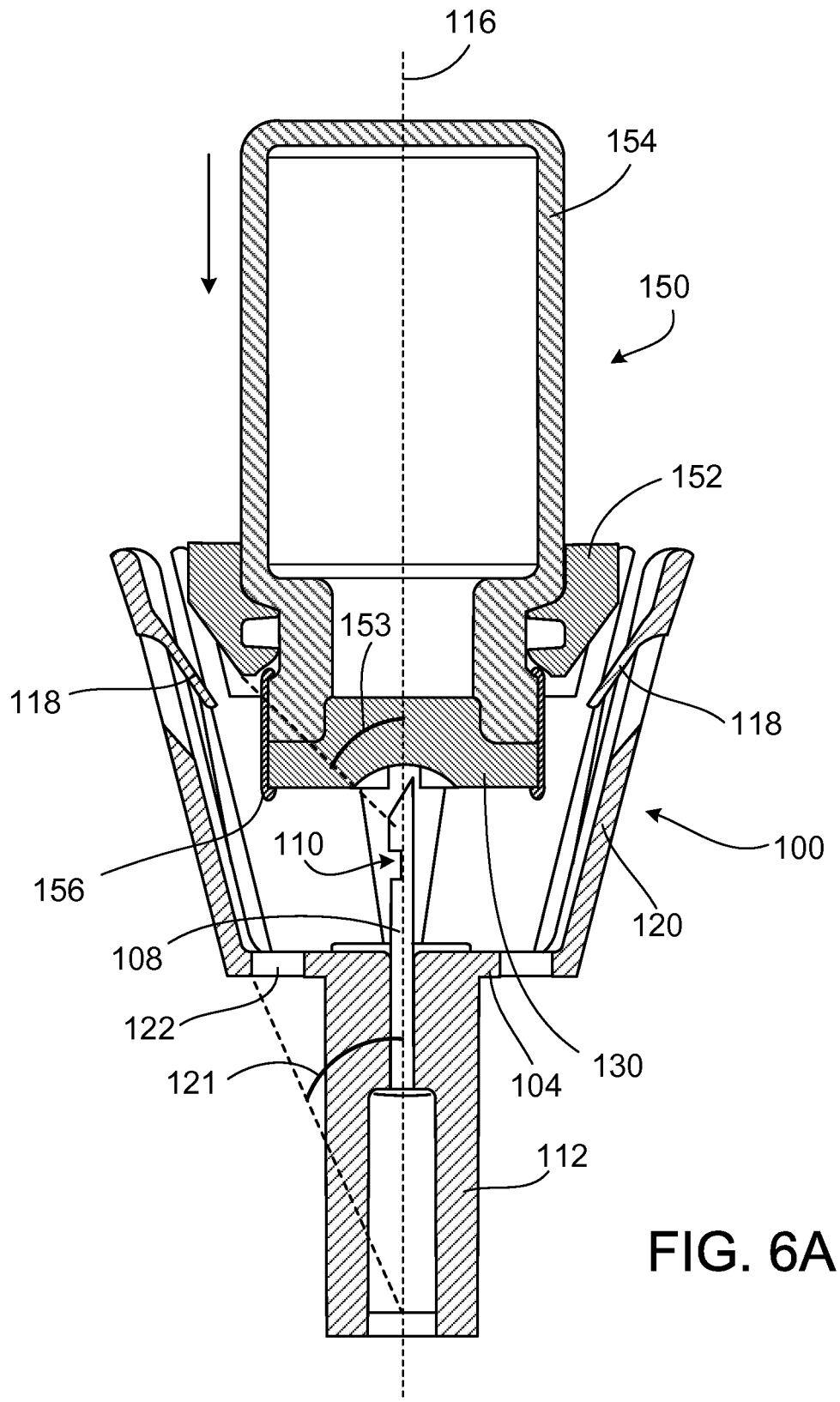
FIGS. 6A-6F are sequential cross-sectional views of a drug vial being inserted into the drug vial spiking device of FIG. 1.

Briefly referring to FIG. 6A, the surface of the vial collar 152 extends at an angle 153 relative to the longitudinal axis 116 when the vial 150 is inserted into the vial spiking device 100. When a drug vial 150 is inserted into the drug vial spiking device 100, the surface of the vial collar 152 contacts the lower portion 120 of each side wall segment 114 and the inclined interface between the lower portion 120 and the vial collar 152) generates an inward and upward (e.g., away from the base 104) force against the vial collar 152 as it is inserted. The lower portion 120 (e.g., the relative angle between the angles 121, 153) is configured to generate a force that is suitable to move the vial 150 upward against the under sides of the fingers 118 and deflect the fingers 118 upward once the fingers 118 have rebounded and the user has released the vial. For example, the lower portions 120 are typically positioned relative to the longitudinal axis 106 at the same angle as the other portions of the side wall segments 114 (i.e., the angle 121). Arranging the lower portions 120 at the same angle as the other portions of the side wall segments 114 has been found to generate suitable resisting forces when the drug vial 150 is inserted into the drug vial spiking device.

Referring back to FIGS. 1 and 2, the base 104 of the drug vial spiking device 100 includes six ventilation holes 122 spaced substantially evenly around the spike 108. The holes 122 are configured to allow gases (e.g., sterilization gases) to pass through the base 104 and surround the spike 108. As shown, the number of holes 122 correlates with the number of side wall segments 114 arranged around the base 104, and the holes 122 are typically aligned with the side wall segments 114 (e.g., aligned with the fingers 118 extending from the side wall segments 114). In addition to allowing gases to permeate through the base 104, due to their alignment with the fingers 118, the holes 122 may also serve as openings through which mold pins that form the back side of the fingers 118 can pass during manufacturing of the drug vial spiking device.

The base 104, sidewall 102, and fingers 118 are typically formed of the same material (e.g., an injection molded material). The material is typically strong enough to withstand forces generated during spiking of the rubber seal while also being resilient so as to permit the fingers 118 and the lower portion 120 to deflect and rebound. The drug vial spiking device 100 can be formed of certain medical grade plastics (e.g., polycarbonate, acrylonitrile butadiene styrene (ABS), polypropylene (PP), polyvinyl chloride (PVC), and other suitable plastics) or other suitable materials.

Figure 3:
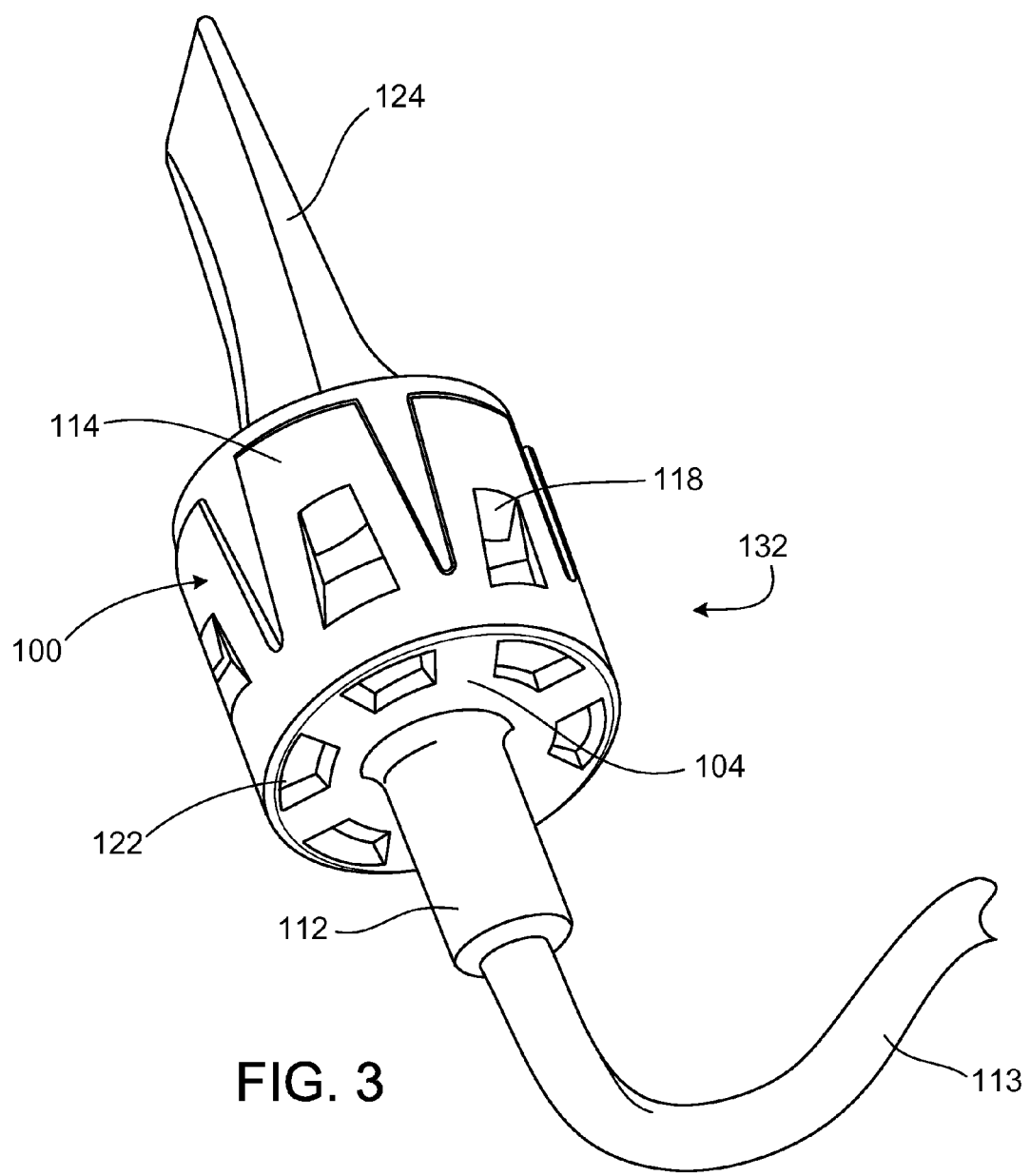
FIG. 3 is a perspective view of a drug vial spiking assembly that includes a spike cover disposed on a spike of the drug vial spiking device of FIG. 1.
Figure 4:
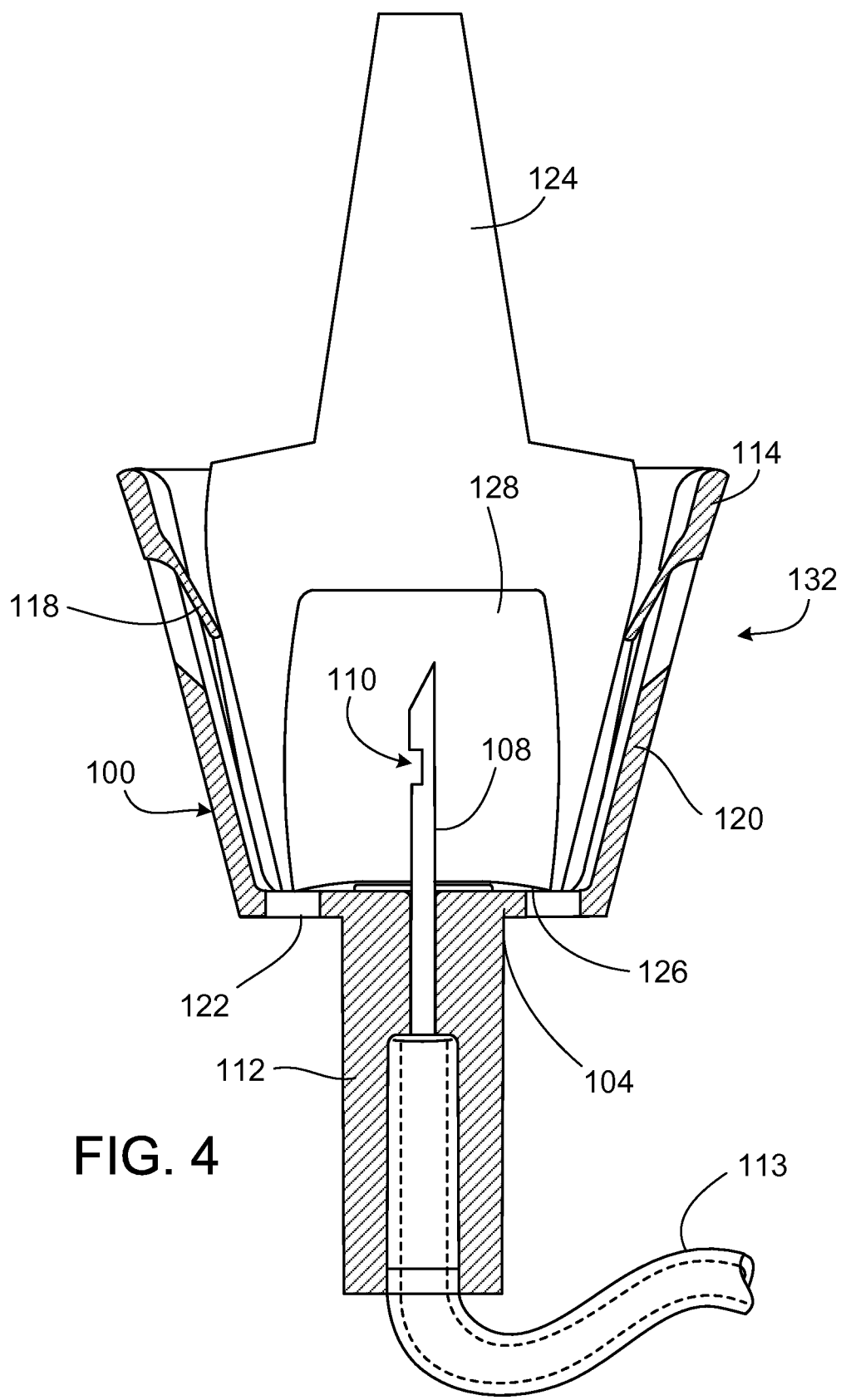
FIG. 4 is a cross-sectional view of the drug vial spiking assembly of FIG. 3.

As shown in FIGS. 3 and 4, the drug vial spiking device 100 is typically provided to the user as part of a vial spiking assembly 132 that includes a spike cover 124 placed into the recess 106 of the drug vial spiking device 100 to cover the spike 108. The spike cover 124 can help prevent objects from contacting and contaminating the spike 108 prior to use and can also prevent users from inadvertently sticking themselves with the spike 108. The spike cover 124 is configured to be received in the drug vial receiving recess 106 and temporarily retained by the fingers 118 and/or the side wall segments 114. For example, the spike cover can be retained via a loose interference fit. The fingers 118 and/or the side wall segments 114 provide a resisting force of about 0.75 lbf to about 2 lbf to retain the spike cover 124 when it is retained by the drug vial spiking device 100, but do not significantly deform when the spike cover 124 is inserted into or removed from the drug vial spiking device 100. While the fingers 118 and/or the side wall segments 114 provide a force to retain the spike cover 124, they do not lockingly engage any mating features of the spike cover 124. As a result, the spike cover 124 can be removed without damaging or altering the drug vial spiking device.

As shown in FIG. 4, the spike cover 124 defines an opening 126 extending into an inner cavity 128 that is configured to permit a fluid (e.g., a gas) to enter and exit the cavity 128 by passing substantially only through the opening 126. When the spike cover 124 is retained by the drug vial spiking device 100, the spike cover 124 covers the spike 108 of the drug vial spiking device 100 in a manner so that fluid can substantially only enter and exit the recess 106 of the drug vial spiking device 100 through the holes 122 in the base 104 of the drug vial spiking device 100.

The spike cover 124 is typically made from one or more suitable gas-impermeable materials. Examples of such materials include plastics (e.g., polycarbonate, acrylonitrile butadiene styrene (ABS), polypropylene (PP), polyvinyl chloride (PVC), and other suitable plastics) or suitable metals.

The spike cover 124 can be formed by any of various suitable manufacturing techniques, such as molding, casting, machining, or other techniques.

Sterilization Process

Figure 5:
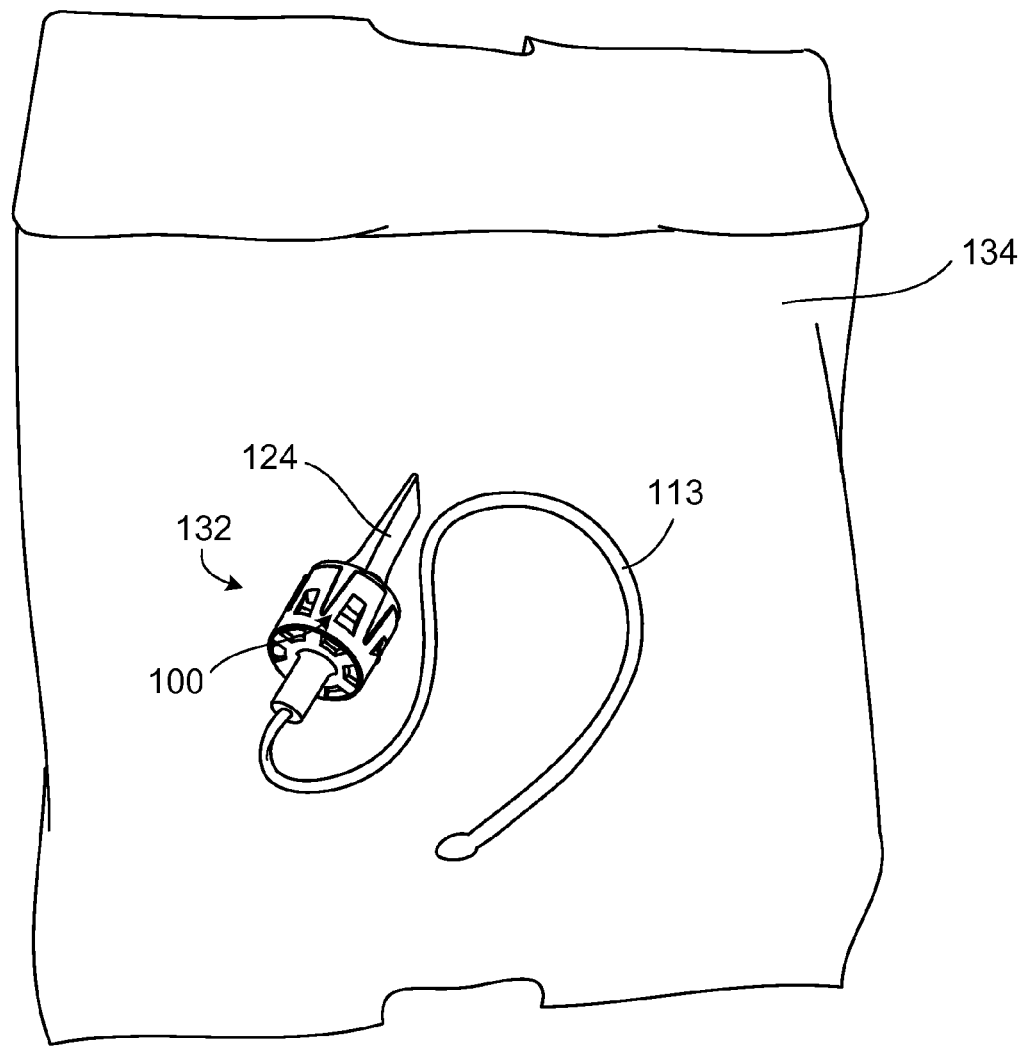
FIG. 5 is a perspective view of the drug vial spiking assembly of FIG. 3 connected to a drug delivery line and packaged for sterilization.

After the drug vial spiking device 100 is manufactured, it can be packaged and sterilized for use in a drug delivery system. FIG. 5 illustrates the vial spiking assembly 132 packaged in a bag 134.

The bag 134 is typically formed of two different materials that are bonded together. For example, one side of the bag can be formed of a gas-impermeable plastic material (e.g., polyethylene (PE) or polypropylene (PP)) and the other side of the bag can be formed of a more permeable material, such as Tyvek® so that a fluid, such as a sterilizing gas (e.g., ethylene oxide gas) can pass into and out of the bag 134.

To sterilize the bag 134 and the vial spiking assembly 132, the bag 134 containing the drug vial spiking device assembly 132 is placed in a chamber or vessel and subjected to a pressurized sterilizing gas entering the chamber. The sterilizing gas can, for example, be pressurized and the pressure can be increased at a pressure ramp rate of about 1.5 psi/minute. The sterilizing gas permeates through the permeable material of the bag, passes through the holes 122 in the base 104 of the drug vial spiking device 100, and surrounds and sterilizes the spike 108. The holes 122 in the drug vial spiking device 100 permit the sterilization gases to surround the spike 108 without requiring the use of potentially costly filters arranged in the drug vial spiking device 100 or the spike cover 124.

Once sterilized by the sterilizing gas, the spike cover 124 reduces the likelihood that the spike 108 will be contaminated. For example, when the drug vial spiking device assembly 132 is removed from the bag, the spike cover 124 reduces the likelihood that the spike 108 will inadvertently be touched or otherwise contacted (e.g., by the user or by airborne particles, such as spittle).

This sterilization process is typically performed after packaging and before shipping to consumer.

Method of Use

The drug vial spiking device 100 can be used with a variety of drug delivery devices, such as a drug delivery device of a dialysis system (e.g., a hemodialysis system). Prior to use, the bag 134 is opened so that the vial spiking assembly 132 can be removed for use. The vial spiking assembly 132 is then removed and the bag 134 is discarded. The drug delivery line 113 is then attached to a fluid line set that is fluidly connected (either directly or via another fluid line set, such as an extracorporeal blood line set) to a patient for delivering liquid (e.g., drug) to the patient. The spike cover 124 is then removed from the drug vial spiking device 100 so that a vial 150 can be spiked by inserting the vial 150 into the recess 106 of the drug vial spiking device 100.

As shown in FIG. 6A, the vial 150 is then inserted into the drug vial spiking device 100. The vial 150 includes a bottle 154 and a seal 130 that is compressed between a cap 156 and a top surface of the bottle 154 to limit the extent to which the seal 130 can move relative to the bottle 154 when spiked. The vial 150 also includes a collar 152 disposed around a neck of the bottle 154.

Figure 6B:
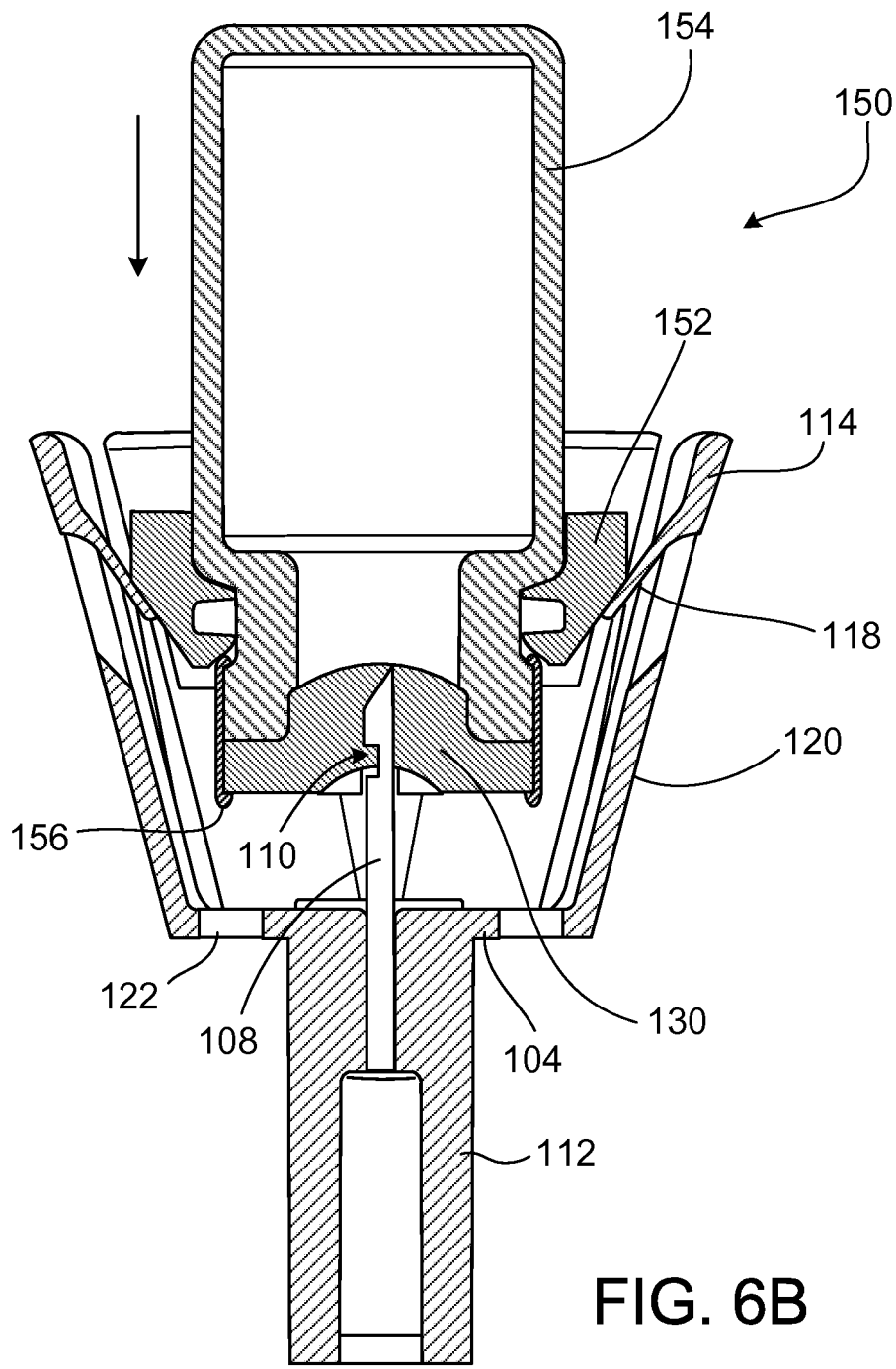
Figure 6C:
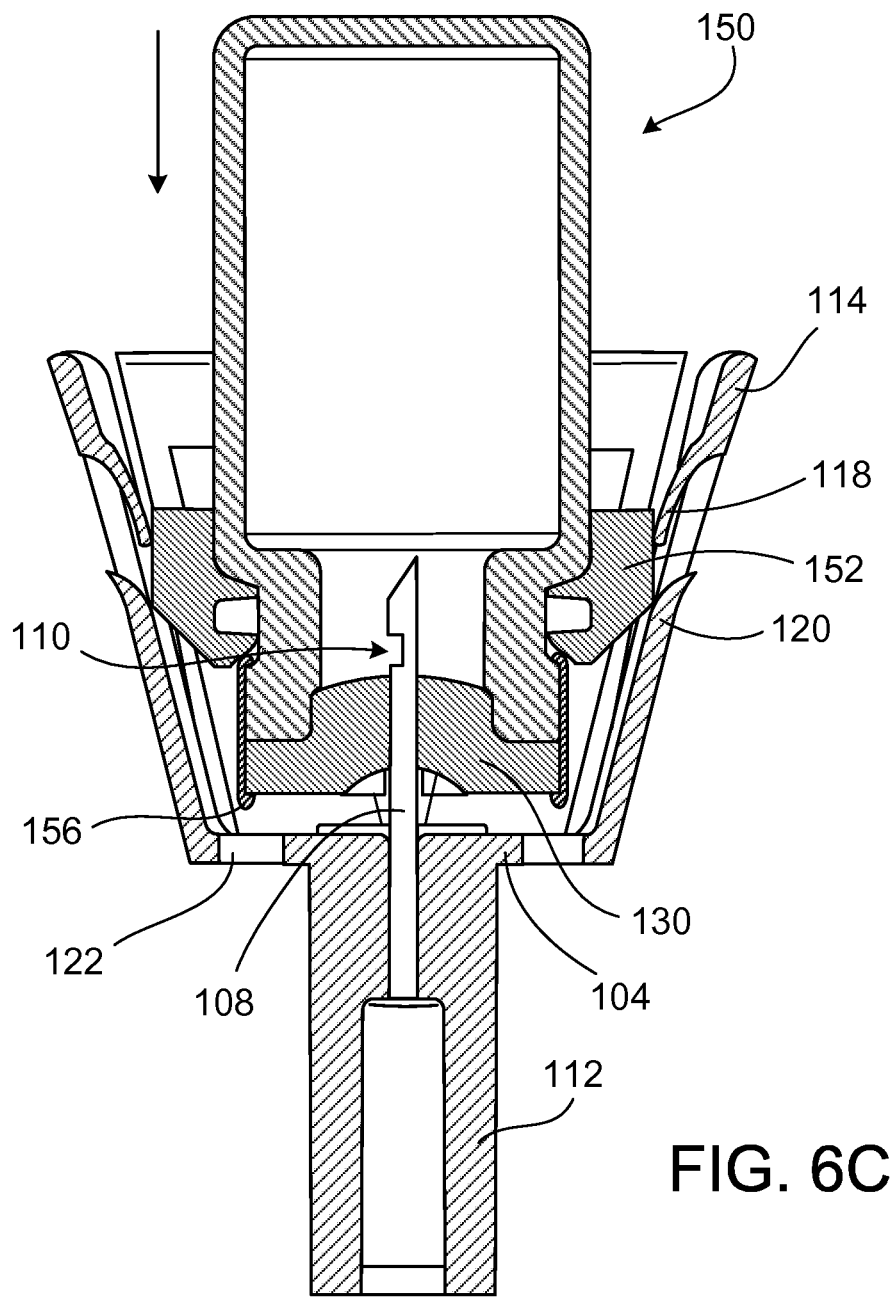

Referring to FIG. 6B, once the vial 150 is inserted a certain distance, the collar 152 disposed around the bottle 154 of the vial 150 contacts a first side of the fingers 118 (i.e., the upward facing side of the fingers 118 in the view shown in FIG. 6B). As the vial 150 is inserted further into the drug vial spiking device, the fingers 118 provide an opposing force to the collar 152 as they are deflected downward and outward.

As the vial 150 is inserted further into the drug vial spiking device 100, the spike 108 begins to penetrate the rubber seal 130 of the vial 150. Due to friction between the spike 108 and the rubber seal 130, the rubber seal 130 deflects upward relative to the other components of the vial 150, forming a convex surface on the inside of the vial 154.

Referring to FIG. 6C, in addition to the fingers 118, the lower portions 120 of the side wall segments 114 provide an additional opposing, upward force against the collar 152 as the lower portions 120 of the side wall segments 114 are contacted and deflect. This force increases as the vial 150 is inserted further into the drug vial spiking device 100 (i.e., as the inner diameter of the lower portions 120 of the tapered side wall segments 114 contacted by the collar 152 decreases).

Figure 6D:
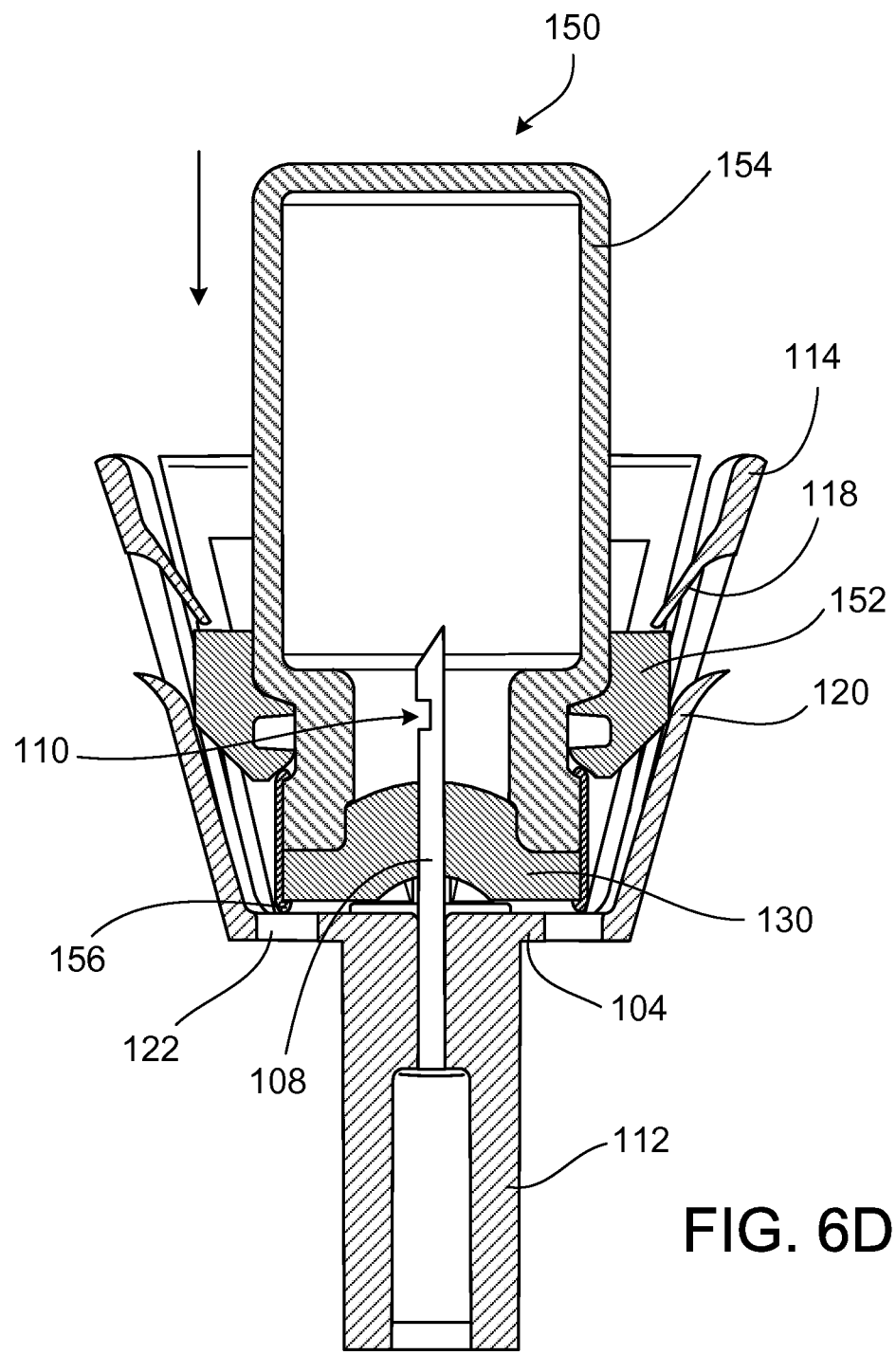

As shown in FIG. 6D, as the vial 150 is inserted further into the drug vial spiking device 100, the fingers 118 provide the opposing force until the collar 152 clears the fingers 118 and the fingers 118 rebound towards the longitudinal axis 116. In some implementations, the fingers 118 produce an audible indication (e.g., a clicking or snapping sound) to indicate that the collar 152 has cleared the fingers 118 and they have rebounded and are above the collar 152.

Figure 6E:
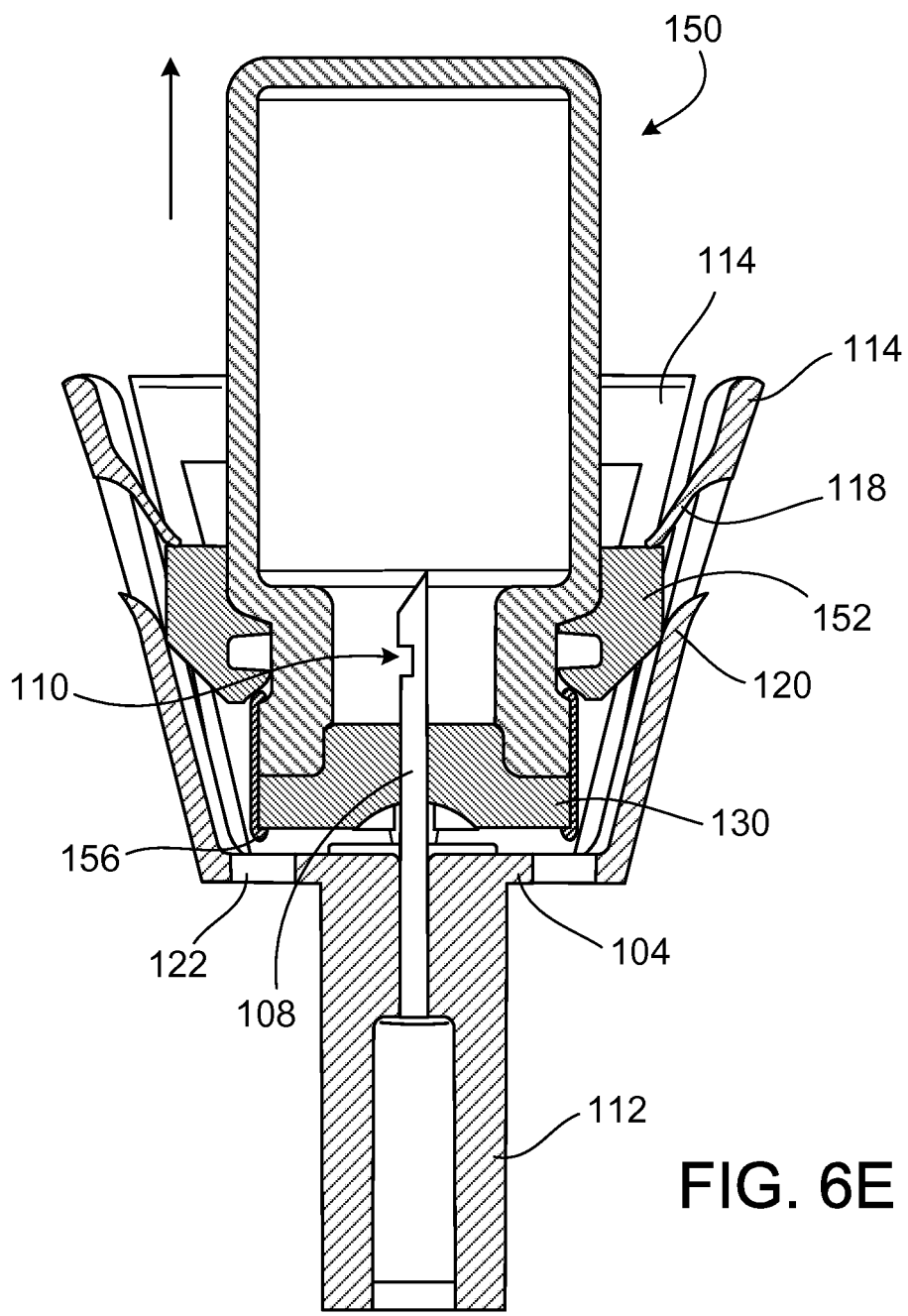

Once the fingers 118 rebound, the vial 150 can be released by the user. As shown in FIG. 6E, the upward force generated by the lower portions 120 pushes the collar 152 (and therefore the rest of the vial 150) away from the base 104 and into the fingers 118 after the vial 150 has been released by the user. The fingers 118 provide resistance as the vial 150 moves upward.

Figure 6F:
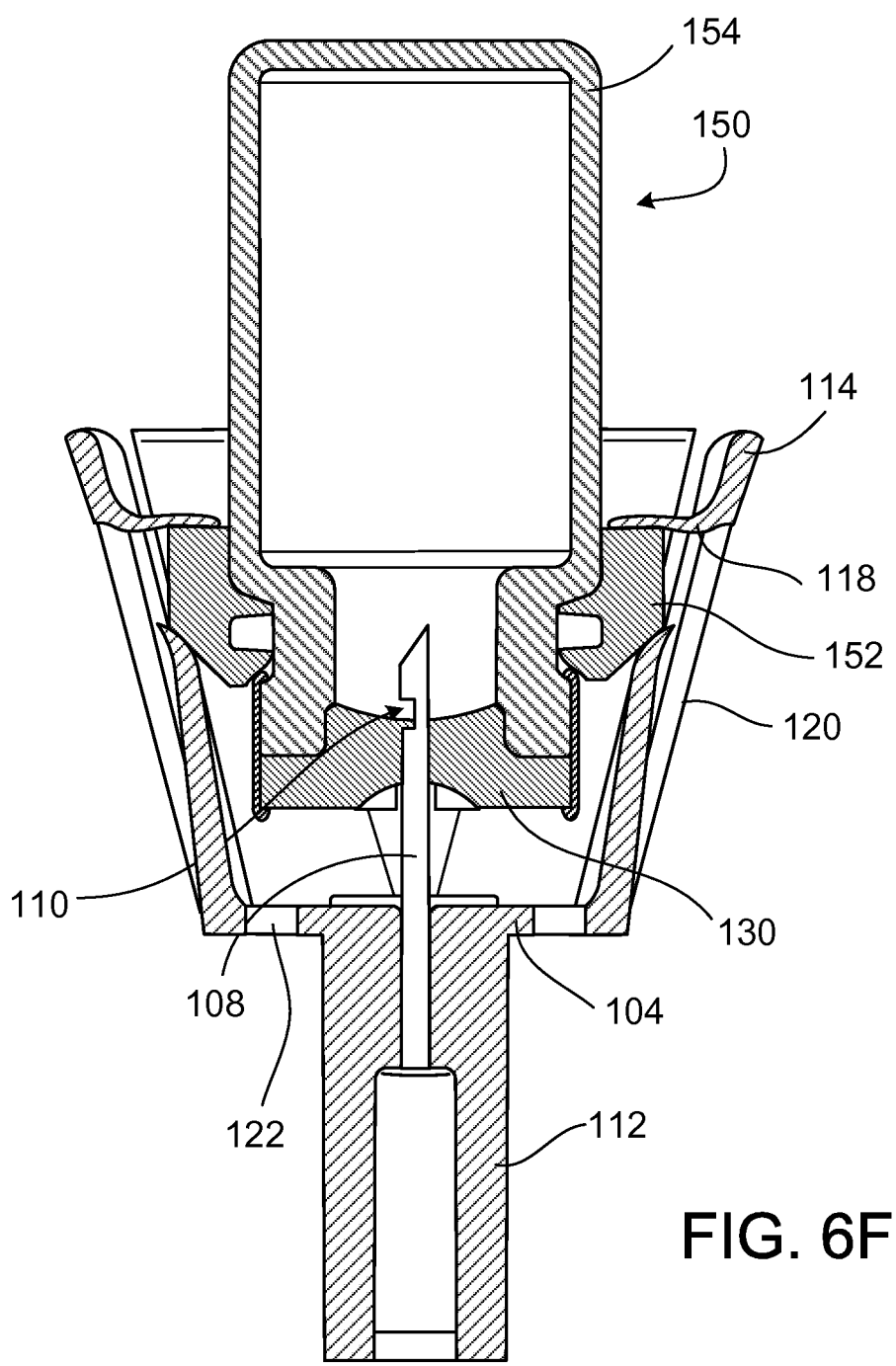

The lower portions 120 force the vial 150 upwards until the fingers 118 are deflected upward a certain distance as a result of the moving vial 150, as shown in FIG. 6F. The fingers 118 deflect upward until they are about parallel to the base 104 and an upper surface on the collar 130. At this point, resistance provided by the fingers 118 is greater than the upward force provided the side wall 102. Therefore, the vial stops moving upward.

Similar to when the vial 150 is inserted into the drug vial spiking device 100, when the vial 150 moves away from the base 104, friction between the spike 108 and the rubber seal 130 causes the rubber seal 130 to deflect. The fingers 118 and the lower portions 120 are configured to permit the vial 150 to move a distance upward that is large enough so that the rubber seal 130 no longer forms a convex surface inside the vial. The lower portions typically force the vial 150 away from the base 104 far enough so that the rubber seal 130 deflects to form a concave surface inside the vial 150. The concave surface helps to increase the likelihood that any liquid (e.g., drug) remaining inside the vial 154 will flow down the rubber seal 130 to a lowermost region of the rubber seal 130 and into the spike 108 for use. As shown in FIG. 6F, the top surface of concave portion of the rubber seal 130 is typically aligned with (i.e., at the same vertical position as) the side-opening 110 of the spike 108 so that fluid can flow from the top of the rubber seal 130 and into the spike 108.

Alternative Embodiments

Figure 7:
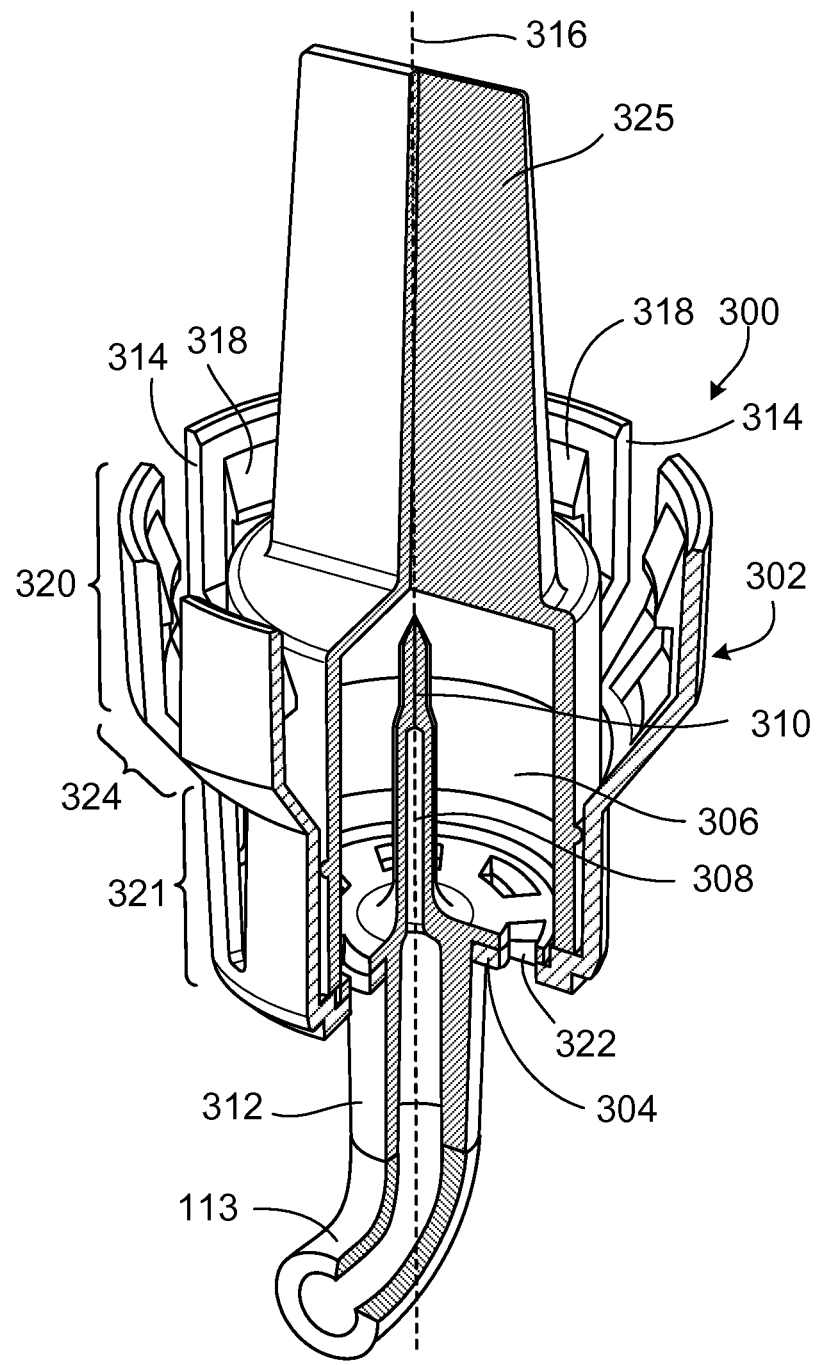
FIG. 7 is a cut-away view of a drug vial spiking assembly that includes a spike cover disposed on a spike of a drug vial spiking device that includes a side wall segments that extend at different angles along their lengths relative to a longitudinal axis of the spiking device.
Figure 8:
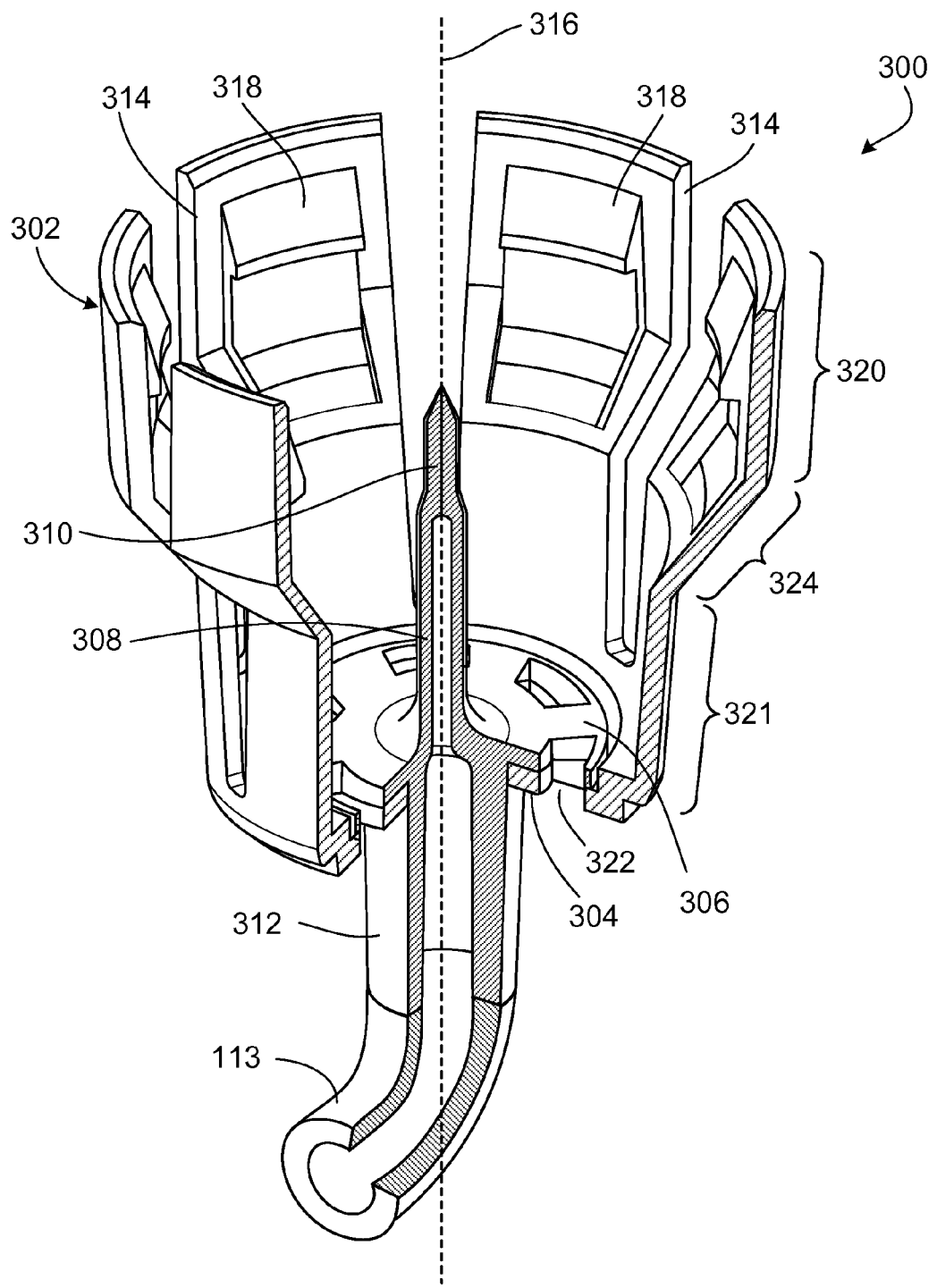
FIG. 8 is a cut-away view of the drug vial spiking device of FIG. 7.

While the side wall segments 114 of the spiking device 100 have been described and illustrated as extending at a substantially contstant acute angle relative to the longitudinal axis 116 along their entire length (i.e., from the base 104 to the opposite free ends of the side wall segments 114) when in an undeformed state, in some implementations, the angles at which the side wall segments extend relative to the longitudinal axis vary along the lengths of the side wall segments. FIGS. 7 and 8, for example, show a spiking device 300 having a side wall 302 configured in this way. FIG. 7 shows a cut-away view of a spiking assembly that includes the spiking device 300 and a spike cover 325 that is disposed in a drug vial receiving recess 306 of the spiking device 300. The spike cover 325 covers a spike 308, which extends upward from a central region of a base 304 of the spiking device 300 and has a central passage in fluid communication with a side-opening 310 of the spike 308. This is how the spiking device 300 would typically be provided to a consumer. FIG. 8 shows a cut-away view of the spiking device 300 after the spike cover 325 has been removed from the spiking device 300.

Referring to FIGS. 7 and 8, the side wall 302 extends from a peripheral region of the base 304 to form the drug vial receiving recess 306. The side wall 302 includes six side wall segments 314 that are circumferentially spaced along the side wall 302. Each of the side wall segments 314 includes an upper region 320 and a lower region 321 that extend substantially parallel to a longitudinal axis 316 of the spiking device 300 (i.e., substantially perpendicular to the base 304) and a middle region 324 that extends at an acute angle relative to the longitudinal axis 316. In some implementations, the upper and lower regions 320, 321 of the side wall segments 314 extend at an angle of 35 degrees to 37 degrees (e.g., about 36 degrees) relative to the longitudinal axis 316, and the middle regions 324 of the side wall segments 314 extend at an angle of 29 degrees to 31 degrees (e.g., about 30 degrees) relative to the longitudinal axis 316. Typically, the upper and lower regions 320, 321 of the side wall segments 314 have a length of 0.25 inch to 0.35 inch, and the middle regions 324 of the side wall segments 314 have a length of 0.15 inch to 0.25 inch.

The side wall segments 314 are configured to deflect away from the longitudinal axis 316 of the drug vial spiking device 300 when a radially outward force is applied to the side wall segments 314 (e.g., as a result of a drug vial being inserted into the recess 306) and rebound towards the longitudinal axis 316 when the force is released. In particular, as a drug vial is inserted into the recess 306, a surface of the vial (e.g., a surface of a collar of the vial) would contact the angled middle portions 324 of the side wall segments 314 causing the side wall segments 314 to deflect radially outwardly. Due to the shorter angled surface of the middle portions 324 (as compared to the length of the angled side wall segments 114 described above), the vial is allowed to bottom out (i.e., contact the base 304) faster and with less applied force. The side wall segments 314 are resilient and thus force the vial upward (i.e., away from the base 304) as the downward force applied to the vial is released and the side wall segments 314 rebound radially inward.

Still referring to FIGS. 7 and 8, each side wall segment 314 includes a retaining finger or projection 318 that extends radially inward from the side wall segment 314 (i.e., toward the longitudinal axis 316). An upper surface of each finger 318 extends at an acute angle (e.g., an angle of 10 degrees to 30 degrees, about 20 degrees) relative to the longitudinal axis 316. The fingers 318 are sized so that when the drug vial has been fully inserted into the recess 306, the fingers 318 can contact an upward facing surface of the vial (i.e., the bottom surface of the upside down vial) to retain the vial within the recess 306. Each of the fingers or projections 318 is rigidly fixed to its associated side wall segment 314. However, it should be appreciated that the fingers 318 could alternatively be cantilevered in a manner similar to the fingers 118 of the spiking device 100 so that the fingers 318 can move radially inward and outward relative to the side wall segments 314.

The central passage of the spike 308 is in fluid communication with the side opening 310 and with an outlet boss 312 extending from a bottom surface of the base 304. The outlet boss 312 is configured to connect to a drug delivery line 113 that can be used to deliver drug from the spiked drug vial to a patient during treatment. In the illustrated embodiment, the spike 308 is formed separately from the base 304 and then attached (e.g., thermally bonded or adhesively bonded) to the base 304. The base region of the spike 308 and the base 304 include apertures that align with one another to form vent openings 322 that allow the gases to vent through the base 304 during a sterilization process, as discussed above with respect to spiking device 100. The base 304 also includes an opening that aligns with the central passage of the spike 308 to allow fluid to pass through the spike 308 to the drug delivery line 113. In other embodiments, the spike 308 can be integrally formed with the base 304 in a manner similar to that discussed above with respect to the spiking device 100. The spiking device 300 can be formed of any of the various materials and using any of the various techniques discussed above with respect to the spiking device 100.

Like the drug vial spiking device 100 discussed above, the drug vial spiking device 300 can be used with a variety of drug delivery devices, such as a drug delivery device of a dialysis system (e.g., a hemodialysis system). The method of using the drug vial spiking device 300 is generally the same as the method of using the drug vial spiking device 100 discussed above and will be briefly described below.

Figure 9A:
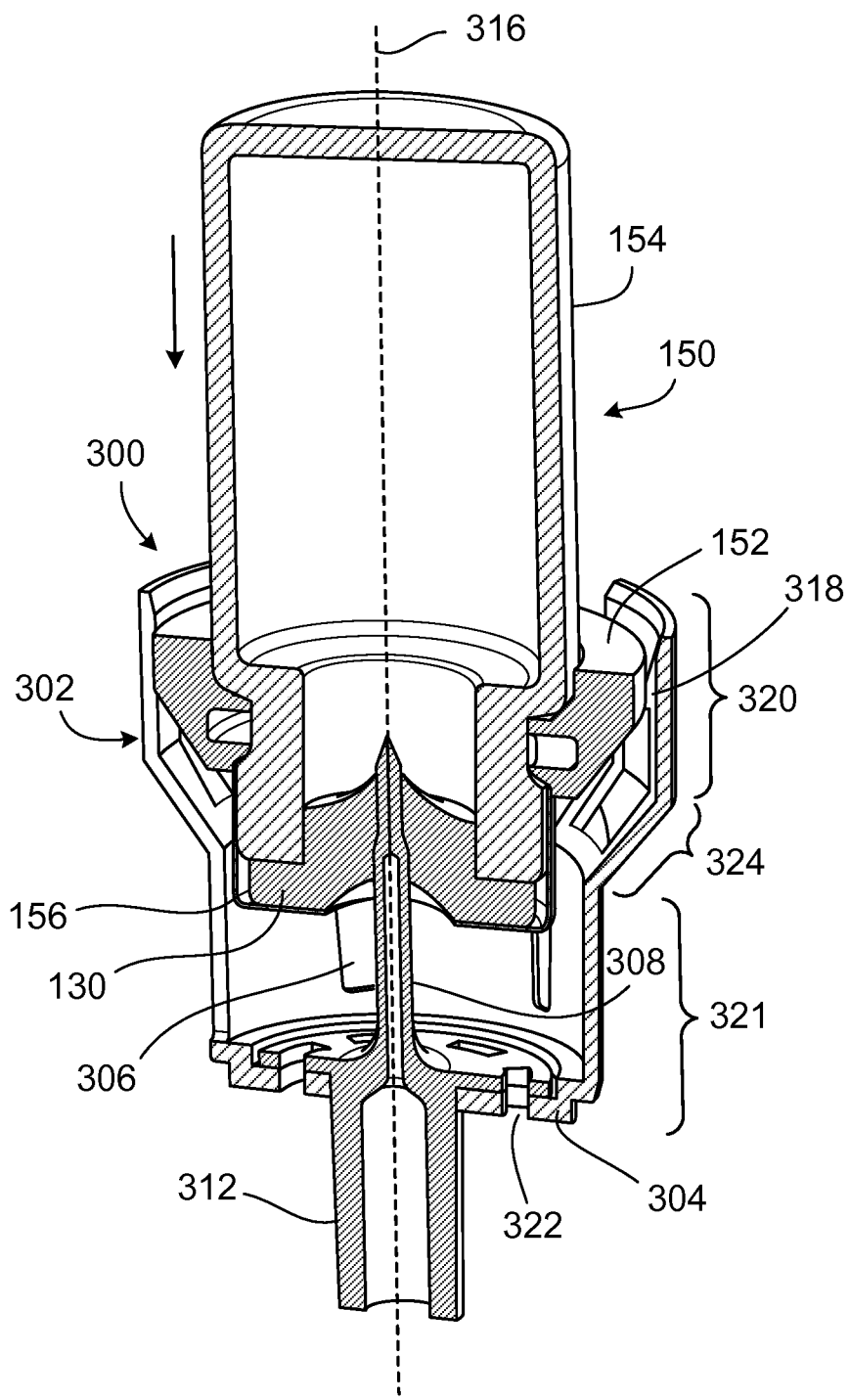
FIGS. 9A-9C are sequential cross-sectional views of a drug vial being inserted into the drug vial spiking device of FIGS. 7 and 8.

Referring to FIG. 9A, after the spike cover 325 has been removed from the drug vial spiking device 300, the vial 150 is inserted into the recess 306 of the drug vial spiking device 300. During the initial stage of insertion, the spike 308 of the spiking device 300 pierces the rubber seal 130 of the vial 150, and the collar 152 that is disposed around the neck of the bottle 154 of the vial 150 contacts the fingers 318 of the spiking device 300. As the user continues to push the vial 150 downward into the recess 306, the collar 152 of the vial 150 rides along the fingers 318 and causes the side wall segments 314 to deflect radially outward, allowing the collar 152 to slide past the fingers 318.

Figure 9B:
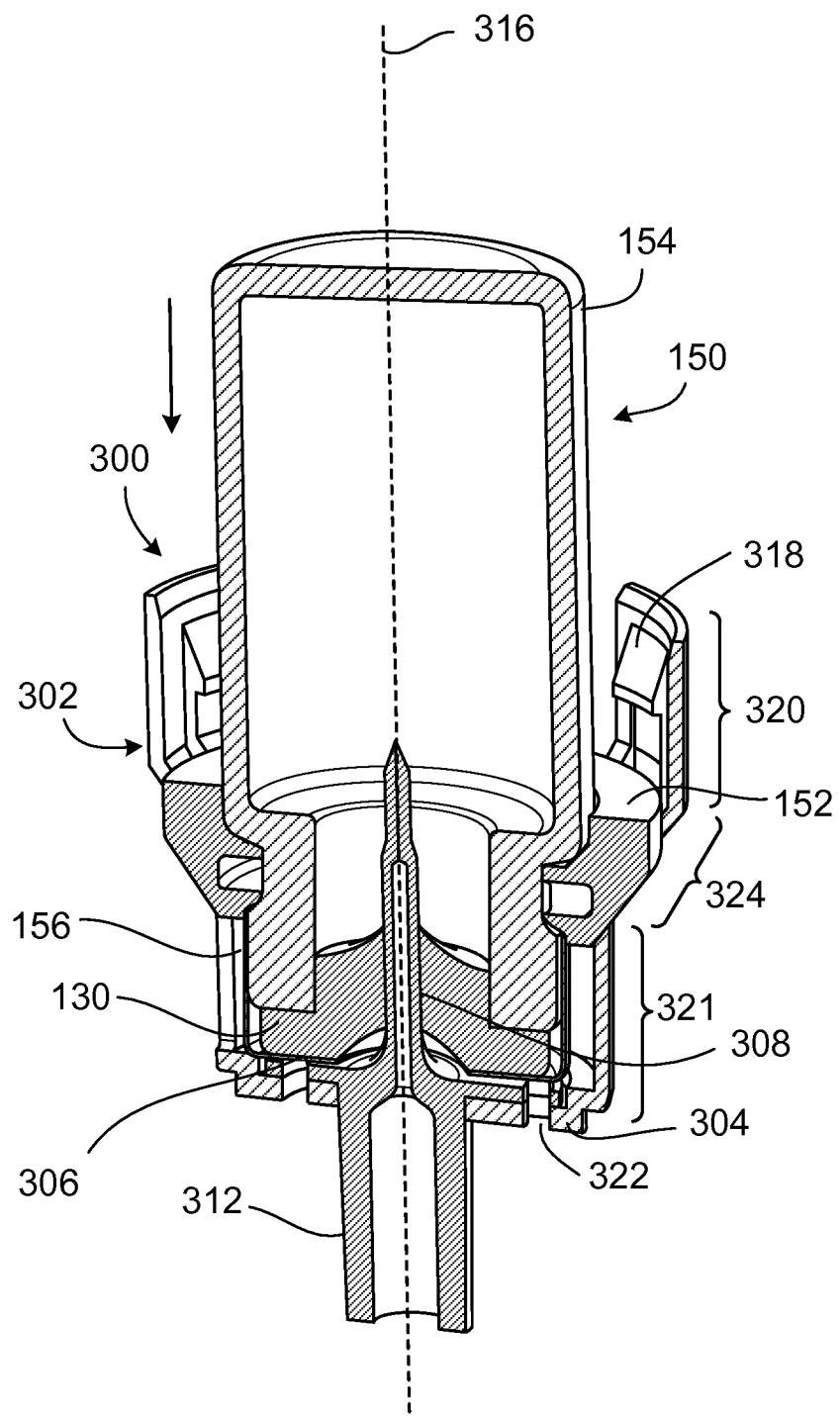

Referring to FIG. 9B, as the vial 150 is inserted further into the drug vial spiking device 100, friction between the spike 308 and the rubber seal 130 causes the rubber seal 130 to deflect upward relative to the other components of the vial 150, forming a convex surface on the inside of the vial 154. Additionally, due to the angled geometry of the middle portions 324 of the side wall segments 314 and the collar 152 of the vial 150, the collar 152 causes the side wall segments 314 to deflect radially outward as the vial 150 is pushed further into the recess 306 of the spiking device 300. The outward radial deflection of the side wall segments 314 permits the vial 150 to be pushed all the way into the recess 308 until the vial 150 bottoms out (i.e., until the cap 156 of the vial 150 contacts the base 304 of the spiking device 300). It has been found that the relatively short angled middle portions 324 of the side wall segments 314 allow the side wall segments 314 to deflect radially outward more quickly and with less resistance than the side wall segments 114 of the spiking device 100 described above. As a result, the vial 150 can be fully inserted into the recess 308 of the spiking device 300 more quickly and with less force than the vial 150 can be fully inserted into the recess 108 of the spiking device 100 described above.

Figure 9C:
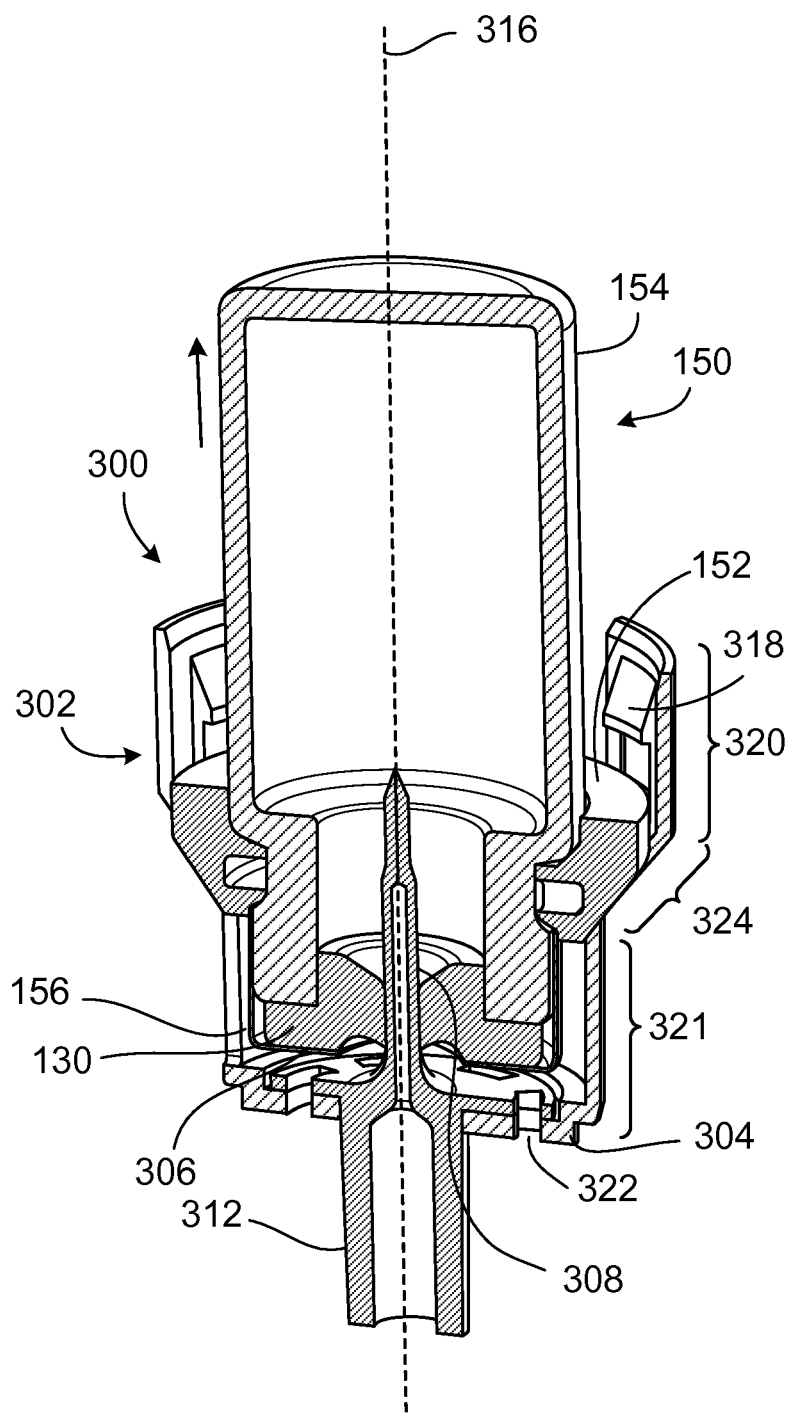

After the vial 150 has been fully inserted into the recess 308 of the spiking device 300 (i.e., after the cap 156 of the vial 150 contacts the base 304 of the spiking device 300), the user releases the vial 150. As shown in FIG. 9C, the upward forces generated as the middle portions 324 of the resilient side wall segments 314 rebound radially inward push the collar 152 (and therefore the rest of the vial 150) away from the base 304 after the vial 150 has been released by the user. Friction between the spike 308 and the rubber seal 130 of the vial 150 causes the rubber seal 130 to deflect. The middle portions 324 of the side wall segments 314 are configured to push the vial 150 upward a sufficient distance so that the rubber seal 130 no longer forms a convex surface inside the vial 150. The middle portions of the side wall segments 314 typically force the vial 150 away from the base 304 far enough so that the rubber seal 130 deflects to form a concave surface inside the vial 154, as shown in FIG. 9C. As discussed above, the concave surface increases the likelihood that any liquid (e.g., drug) remaining inside the vial 150 will flow down the rubber seal 130 to a lowermost region of the rubber seal 130 and into the spike 308 for delivery to the patient.

Figure 10:
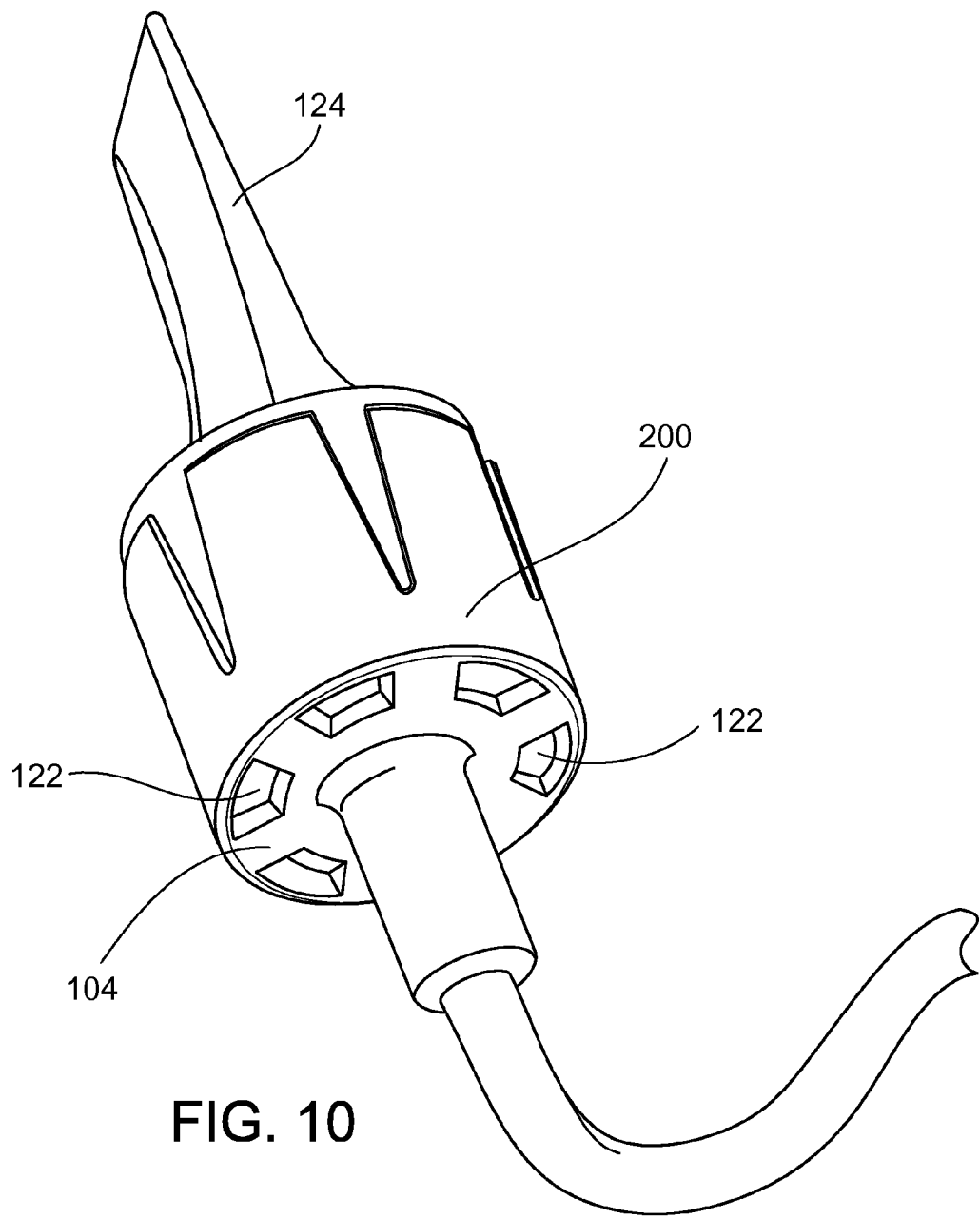
FIG. 10 is a perspective view of another drug vial spiking device including a base with ventilation holes.

While the drug vial spiking devices discussed above have been described as having fingers and side wall segments that generate resisting forces as the vial is inserted into the drug vial spiking device, other configurations are possible. For example, FIG. 10 illustrates a drug vial spiking device 200 that is generally the same as the vial spiking device 100 described above but does not include resilient fingers 118 or lower side wall segment portions 120 that deflect the seal of the drug vial relative to the spike. Like the drug vial spiking device 100, the drug vial spiking device 200 includes ventilation holes 122 that allow gases (e.g., sterilization gas) to pass through the base 104 and surround a spike, for example, during sterilization.

While the bases of the drug vial spiking devices discussed above have been described as each having six holes arranged around the spike that align substantially with the side wall segments, other configurations are possible. For example, in some implementations, each base has more (e.g., seven, eight, nine, ten, or more) or fewer (e.g., five, four, three, two, one) holes. In some implementations, the holes do not align with the side wall segments. Alternatively, in some implementations, the base includes a mesh-like structure having many holes.

While the holes in the drug vial spiking devices above have been described as being formed along the base, other configurations are possible. For example, in some implementations, the holes are formed along portions of the side wall segments. Alternatively, in some implementations, the drug vial spiking device does not include such ventilation holes.

While the drug vial spiking devices discussed above have been described as including ventilation holes, those spiking devices could alternatively include no ventilation holes. In implementations in which the spiking device includes no ventilation holes, the spiking device can be provided with a gas-permeable spike cover rather than a gas impermeable spike cover. In order to sterilize the spiking device, a gas can be passed through the central passage of the spike in the manner discussed above. However, rather than exiting the spiking device via holes in the spiking device (e.g., via holes in the base or sidewall of the spiking device), the ventilation gases would pass through the gas permeable spike cover.

While the side walls 102, 302 of the spiking devices 100, 200, 300 discussed above have been described as including six side wall segments, more or fewer side wall segments are possible. For example, in some implementations, the side wall includes two, three, four, five, or more side wall segments.

While the side walls 102, 302 of the spiking devices 100, 300 discussed above have been described as having one or more resilient wall segments that are inclined away from the spike, other configurations are possible. For example, in some implementations, the drug vial spiking device includes a generally vertical non-resilient side wall and the vial includes an inclined and/or resilient portion, such as a collar that can deflect to provide a relative force between the vial and the side wall to move the vial upward away from the base.

While each of the side wall segments 114, 314 of the spiking devices 100, 300 discussed above has been described as having one retaining finger or projection 118, 318, other configurations are possible. For example, in some implementations, only some of the side wall segments have fingers. In some implementations, each side wall segment has more (e.g., two, three, four, or more) or fewer (e.g., zero) fingers.

While the fingers 118 of the spiking device 100 have been described as being substantially parallel to the base when the vial stops moving away from the base during spiking, other configurations are possible. For example, in some embodiments, the fingers are inclined towards the base when the vial stops moving outward.

While the drug vial spiking devices 100, 300 have been described as having side wall segment portions that provide an upward force against the vial, other configurations are possible. For example, in some implementations, other types of resilient members (e.g., springs, compressible foam pieces, flexible fingers arranged along the base, or other members) are additionally or alternatively attached to base to push vial away from the base.

While the vial and vial spiking devices have been described as having a generally circular cross-section, other shaped vials and/or vial spiking devices are possible. For example, the vial and/or the vial spiking device, in particular, the interface between the vial and the drug vial spiking device, can have other cross-sectional shapes, such as an ellipse, a polygon (e.g., a rectangle, a square, a pentagon, a hexagon, or another polygon), or other structurally suitable shapes.

While some of the drug vial spiking devices have been described as being substantially integral one-piece components, other configurations are possible. For example, one or more portions of the drug vial spiking device (e.g., the base, the spike, the side wall segments, and/or the fingers) can be formed as separate components that can be attached to one another to form the drug vial spiking device.

While many of the drug vial spiking devices have been described as being made from substantially one material, other configurations are possible. For example, in some implementations, different portions of the drug vial spiking device (e.g., the base, the spike, the side wall segments, and/or the fingers) are made from different materials.

In some implementations, a tip region of the spike of the spiking device includes a silicone coating. Such a coating can reduce friction associated with initially piercing the seal of the vial with the spike. Any of various techniques can be used to apply the silicone coating to the tip region of the spike. In certain cases, for example, a dip coating technique is used to coat the tip region of the spike.

While the vial has been described as having a collar that is received by the drug vial spiking device and interfaces with the fingers and the lower surfaces, other configurations are possible. For example, in some implementations, a vial is inserted into the drug vial spiking device and other features or portions of the vial interface with the fingers and lower surfaces of the drug vial spiking device. The cap of the vial can, for example, interface with the fingers and the lower portions to move the vial relative to the base.

While the seal of the drug vial has been described as being a rubber seal, the seal can be made of any or various suitable materials that can be pierced by the spike. For example, the seal can be made from any of various structurally suitable materials, such as rubbers or plastics.

While the drug vial spiking devices have been described as being used with hemodialysis systems, the devices, assemblies, and methods described herein can be used with various other types of drug delivery processes and systems. For example, in some implementations, the drug vial spiking devices are used for delivering drugs during peritoneal dialysis treatments, blood perfusion treatments, intravenous infusion treatments, or other medical fluid handling treatments, such as delivering drugs intravenously.

A number of embodiments have been described. Nevertheless, it will be understood that various modifications may be made without departing from the spirit and scope of the invention. Accordingly, other embodiments are within the scope of the following claims.

What is claimed is:

1. A vial spiking device comprising:
   a base;
   a spike extending from a central region of the base;
   a side wall extending from the base and substantially surrounding the spike, the base and the side wall at least partially defining a recess configured to receive a portion of a vial; and
   a plurality of resilient fingers that extend inwardly from the side wall into the recess, the fingers being spaced circumferentially around the side wall, the fingers being configured so that as the vial is inserted into the recess of the vial spiking device, the fingers deflect toward the side wall and allow the portion of the vial to move beyond the fingers, and the fingers being configured to rebound into the recess after the portion of the vial has moved beyond the fingers,
   wherein the side wall is configured to force the portion of the vial away from the base and into contact with the fingers after the portion of the vial has moved beyond the fingers and the fingers have rebounded into the recess.

2. The vial spiking device according to claim 1, wherein the portion of the vial comprises a collar disposed around a neck portion of a bottle of the vial.

3. The vial spiking device according to claim 1, wherein the portion of the vial comprises a cap of the vial.

4. The vial spiking device according to claim 1, wherein a lower portion of the side wall of the vial spiking device extends at a first angle relative to a longitudinal axis of the vial spiking device, and the portion of the vial has a surface that extends at a second angle relative to the longitudinal axis of the vial spiking device when the portion of the vial is disposed in the recess of the vial spiking device, and the surface of the portion of the drug vial interfaces with the lower portion of the side wall when the vial is moved into the recess beyond the fingers.

5. The vial spiking device according to claim 1, wherein the spike of the vial spiking device is configured so that a seal of the vial is deflected causing an inner surface of the rubber seal to be concave when the vial is forced away from the base and into contact with the fingers.

6. The vial spiking device according to claim 1, wherein the fingers are configured to position the vial so that a region along a rubber seal of the vial is positioned over an opening in the spike as the vial is inserted into the recess of the vial spiking device.

7. The vial spiking device according to claim 1, wherein the base defines a plurality of holes that permit a fluid to flow in and out of the vial spiking device through the base.

8. The vial spiking device according to claim 7, wherein each of the holes is longitudinally aligned with one of the fingers.

9. The vial spiking device according to claim 1, wherein the side wall comprises a plurality of side wall segments that are circumferentially spaced around the side wall.

10. The vial spiking device according to claim 9, wherein each of the side wall segments extends at an acute angle relative to the longitudinal axis of the vial spiking device.

11. The vial spiking device according to claim 1, wherein a region of the side wall adjacent the base has an inner diameter that is smaller than an outer diameter of the portion of the vial.

12. The vial spiking device according to claim 1, wherein the vial is a drug vial.

13. A vial spiking device comprising:
    a base;
    a spike extending from a central region of the base;
    a side wall extending from the base and substantially surrounding the spike, the base and the side wall at least partially defining a recess configured to receive a portion of a vial, the side wall comprising a plurality of resilient circumferentially spaced side wall segments that extend at an acute angle relative to a longitudinal axis of the vial spiking device, the side wall segments being configured to deflect away from the longitudinal axis of the vial spiking device when a force is applied to the side wall segments and then rebound toward the longitudinal axis of the vial spiking device when the force is released; and
    a plurality of resilient circumferentially spaced fingers that extend from the side wall and are biased into the recess, the fingers being configured to deflect toward the side wall when a force is applied to the fingers and then rebound away from the side wall when the force is released, wherein the side wall of the vial spiking device is configured to force the portion of the vial away from the base and into contact with the fingers after the portion of the vial has moved beyond the fingers and the fingers have rebounded into the recess.

14. The vial spiking device according to claim 13, wherein the portion of the vial comprises a collar disposed around a neck portion of a bottle of the vial.

15. The vial spiking device according to claim 13, wherein the portion of the vial comprises a cap of the vial.

16. The vial spiking device according to claim 13, wherein a lower portion of the side wall of the vial spiking device extends at a first angle relative to a longitudinal axis of the vial spiking device, and the portion of the vial has a surface that extends at a second angle relative to the longitudinal axis of the vial spiking device when the portion of the vial is disposed in the recess of the vial spiking device, and the surface of the portion of the drug vial interfaces with the lower portion of the side wall when the vial is moved into the recess beyond the fingers.

17. The vial spiking device according to claim 13, wherein the spike of the vial spiking device is configured so that a seal of the vial is deflected causing an inner surface of the rubber seal to be concave when the vial is forced away from the base and into contact with the fingers.

18. The vial spiking device according to claim 13, wherein the fingers are configured to position the vial so that a region along a rubber seal of the vial is positioned over an opening in the spike as the vial is inserted into the recess of the vial spiking device.

19. The vial spiking device according to claim 13, wherein the base defines a plurality of holes that permit a fluid to flow in and out of the vial spiking device through the base.

20. The vial spiking device according to claim 19, wherein each of the holes is longitudinally aligned with one of the fingers.

21. The vial spiking device according to claim 13, wherein the side wall comprises a plurality of side wall segments that are circumferentially spaced around the side wall.

22. The vial spiking device according to claim 21, wherein each of the side wall segments extends at an acute angle relative to the longitudinal axis of the vial spiking device.

23. The vial spiking device according to claim 13, wherein a region of the side wall adjacent the base has an inner diameter that is smaller than an outer diameter of the portion of the vial.

24. The vial spiking device according to claim 13, wherein the vial is a drug vial.

25. A method comprising:

pushing a portion of a vial into a recess defined by a base and a side wall of a vial spiking device such that resilient circumferentially spaced fingers extending from the side wall of the vial spiking device move radially outward and then, after the portion of the vial has moved beyond the fingers, rebound radially inward; and applying a force to the vial that causes the vial to move away from the base and into contact with the fingers, wherein the force is applied by the side wall of the vial spiking device.

26. The method according to claim 25, wherein the side wall of the vial spiking device forces the vial away from the base so that a seal of the vial is deflected causing an inner surface of the seal to be concave.

27. The method according to claim 25, wherein the fingers align a seal of the vial with an opening in a spike extending from the base of the drug vial spiking device.

28. The method according to claim 25, wherein the fingers are configured to position the vial so that a region along a seal of the vial is disposed along an opening in a spike protruding from the base.

29. The method according to claim 25, wherein the vial is pushed into the recess until the vial contacts the base of the vial spiking device.

30. The method according to claim 25, wherein, when the vial moves away from the base, a collar of the vial contacts an underside of the fingers.

31. The method according to claim 30, wherein the fingers are deflected to be substantially parallel to the base.

32. A vial spiking device comprising:

a base;

a spike extending from a central region of the base; and a side wall extending from the base and substantially surrounding the spike, the side wall having a first portion that extends at a first acute angle relative to a longitudinal axis of the spiking device, a second portion that extends at a second acute angle relative to the longitudinal axis of the spiking device, and a third portion that is positioned between the first and second portions and extends at a third acute angle relative to the longitudinal axis of the spiking device, the base and the side wall at least partially defining a recess configured to receive a portion of a vial;

wherein the third portion of the side wall is configured so that as the vial is inserted into the recess of the vial spiking device, the third portion of the side wall deflects radially outward and allows the portion of the vial to be fully inserted into the recess, and the third portion of the side wall is configured to rebound radially inward and force the vial away from the base when a force applied to the vial to insert the vial into the recess is released.

33. The vial spiking device of claim 32, wherein the third acute angle is greater than the first and second acute angles.

34. The vial spiking device of claim 33, wherein the third acute angle is about 29 degrees to about 31 degrees.

35. The vial spiking device of claim 32, wherein the first acute angle is equal to the second acute angle.

36. The vial spiking device of claim 32, further comprising a plurality of resilient fingers that extend inwardly from the side wall into the recess, the fingers being spaced circumferentially around the side wall, the fingers being configured so that as the vial is inserted into the recess of the vial spiking device, the fingers deflect toward the side wall and allow the portion of the vial to move beyond the fingers, and the fingers being configured to rebound into the recess after the portion of the vial has moved beyond the fingers.

37. The vial spiking device of claim 36, wherein the third portion of the side wall is configured to force the portion of the vial away from the base and into contact with the fingers after the portion of the vial has moved beyond the fingers and the fingers have rebounded into the recess.

38. The vial spiking device of claim 32, wherein the portion of the vial comprises a collar disposed around a neck portion of a bottle of the vial.

39. The vial spiking device of claim 32, wherein the spike of the vial spiking device is configured so that a seal of the vial is deflected causing an inner surface of the rubber seal to be concave when the vial is forced away from the base.

40. The vial spiking device of claim 32, wherein the base defines a plurality of holes that permit a fluid to flow into and out of the vial spiking device through the base.

41. The vial spiking device of claim 32, wherein the side wall comprises a plurality of side wall segments that are circumferentially spaced around the side wall, and the first, second, and third portions of the side wall are portions of one of the plurality of side wall segments.

42. The vial spiking device of claim 32, wherein a region of the third portion of the side wall has an inner diameter that is smaller than an outer diameter of the portion of the vial.

* * * * *